United States Patent
Caron et al.

(10) Patent No.: US 11,131,636 B2
(45) Date of Patent: Sep. 28, 2021

(54) IONIC CONCENTRATION-MEASURING DEVICE FOR MEASURING IN SITU AN IONIC CONCENTRATION OF AN IONIC COMPOUND IN A POROUS MEDIUM SOLUTION AND METHOD THEREFOR

(71) Applicant: HORTAU INC., Levis (CA)

(72) Inventors: Jean Caron, Levis (CA); Rock Chabot, St-Lambert-de-Lauzon (CA); Philippe Saucier, Levis (CA); Yann Périard-Larrivée, Quebec (CA); Frédéric Fortin, Quebec (CA)

(73) Assignee: HORTAU INC., Levis (CA)

( * ) Notice: Subject to any disclaimer, the term of this patent is extended or adjusted under 35 U.S.C. 154(b) by 0 days.

(21) Appl. No.: 16/500,559

(22) PCT Filed: Apr. 3, 2018

(86) PCT No.: PCT/CA2018/050405
§ 371 (c)(1),
(2) Date: Oct. 3, 2019

(87) PCT Pub. No.: WO2018/184101
PCT Pub. Date: Oct. 11, 2018

(65) Prior Publication Data
US 2020/0103350 A1    Apr. 2, 2020

Related U.S. Application Data

(60) Provisional application No. 62/480,587, filed on Apr. 3, 2017.

(51) Int. Cl.
  *G01N 21/85* (2006.01)
  *G01N 21/76* (2006.01)
  (Continued)

(52) U.S. Cl.
  CPC ......... *G01N 21/8507* (2013.01); *G01N 21/76* (2013.01); *G01N 33/24* (2013.01);
  (Continued)

(58) Field of Classification Search
  None
  See application file for complete search history.

(56) References Cited

U.S. PATENT DOCUMENTS 5,065,019 A * 11/1991 Darilek ................. G01N 21/64
                                                        250/301
6,666,068 B2 * 12/2003 Boyd ................... G01N 1/2294
                                                        73/31.07

(Continued)

FOREIGN PATENT DOCUMENTS

DE    19616391    11/1996
DE    10047937    4/2002

(Continued)

OTHER PUBLICATIONS

Riga, et al. "Ionic-Equilibrium Time Inside Ceramic Cups in Unsaturated Porous Media", Soil Science Society of America Journal, vol. 62, No. 3, pp. 574-579 (1998).

(Continued)

*Primary Examiner* — Shawn Decenzo
(74) *Attorney, Agent, or Firm* — Thompson Hine LLP

(57) ABSTRACT

A device for measuring an ionic concentration of an ionic compound in a porous medium solution contained in a porous medium. The device includes a sensing portion, a light source, and a light sensor. The sensing portion is miniaturized and includes a permeable material body defining a measuring cavity therein and is insertable in the porous medium to allow the porous medium solution to diffuse through the permeable material body. The light source illuminates the porous medium solution contained inside the (Continued)

measuring cavity. The light sensor detects a resulting light emanating from the porous medium solution, the resulting light having at least one spectral characteristic indicative of the ionic concentration of the ionic compound in the porous medium solution. There is also provided a method for measuring in situ an ionic concentration of an ionic compound in a porous medium solution contained in a porous medium.

24 Claims, 11 Drawing Sheets

(51) Int. Cl.
    *G01N 33/24*     (2006.01)
    *G01N 21/47*     (2006.01)
    *G01N 21/64*     (2006.01)

(52) U.S. Cl.
    CPC ............ *G01N 2021/4742* (2013.01); *G01N 2021/4769* (2013.01); *G01N 2021/6484* (2013.01); *G01N 2021/8528* (2013.01)

(56) References Cited

U.S. PATENT DOCUMENTS

| | | | | |
|---|---|---|---|---|
| 7,234,362 | B2* | 6/2007 | Shinn, II | G01N 33/24 73/784 |
| 7,927,883 | B2* | 4/2011 | Tuli | G01V 9/00 436/110 |
| 8,340,828 | B2* | 12/2012 | Danieli | A01G 25/16 700/284 |
| 8,444,937 | B2* | 5/2013 | Tuli | G01V 9/00 422/535 |
| 2004/0089079 | A1* | 5/2004 | Engebretson | E21B 49/084 73/863.23 |
| 2006/0158652 | A1* | 7/2006 | Rooney | G01N 21/8507 356/406 |
| 2009/0166520 | A1* | 7/2009 | Tuli | G01V 9/00 250/253 |
| 2010/0194411 | A1* | 8/2010 | Caron | G01V 3/06 324/694 |
| 2010/0283993 | A1* | 11/2010 | Preiner | G01N 21/33 356/51 |
| 2012/0140227 | A1* | 6/2012 | Willuweit | G01J 3/0256 356/413 |

FOREIGN PATENT DOCUMENTS

| | | |
|---|---|---|
| DE | 10121326 | 2/2003 |
| DE | 102004056178 | 6/2006 |
| DE | 102011085749 | 2/2013 |
| EP | 1396722 | 3/2004 |

OTHER PUBLICATIONS

Tuli, et al. "In Situ Monitoring of Soil Solution Nitrate: Proof of Concept", Soil Science Society of America Journal, vol. 73, No. 2, pp. 501-509 (2009).

PCT, Canadian Intellectual Property Office (ISA/CA), International Search Report, International Application No. PCT/CA2018/050405, 3 pages (dated Jun. 28, 2019).

PCT, Canadian Intellectual Property Office (ISA/CA), Written Opinion of the International Searching Authority, International Application No. PCT/CA2018/050405, 3 pages (dated Jun. 28, 2019).

* cited by examiner

IONIC CONCENTRATION-MEASURING DEVICE FOR MEASURING IN SITU AN IONIC CONCENTRATION OF AN IONIC COMPOUND IN A POROUS MEDIUM SOLUTION AND METHOD THEREFOR

CROSS-REFERENCE TO RELATED APPLICATIONS

This application is a national stage filing of International Application No. PCT/CA2018/050405, International Publication No. WO 2018/184101, filed on Apr. 3, 2018, which claims priority to U.S. Provisional Patent Application No. 62/480,587, filed on Apr. 3, 2017. The entire contents of both of these applications are incorporated by reference herein.

TECHNICAL FIELD

The technical field generally relates to an ionic concentration-measuring device for measuring in situ an ionic concentration of an ionic compound in a porous medium solution contained in a porous medium, such as soil. It also relates to a method for measuring in situ an ionic concentration of an ionic compound in a porous medium solution contained in a porous medium.

BACKGROUND

The determination of the concentration of an ionic compound dissolved in a porous medium solution, such as and without being limitative a nitrate concentration, often requires that a sample of the porous medium solution extracted from the porous medium, such as soil, be transported to and measured in a laboratory, i.e. away from the measurement site, and hence provide only information about the ionic concentration at the time the sample was extracted instead of providing a real-time concentration of the ionic compound. Furthermore, during transport, there is a risk to alter the sample and to modify the concentration by a chemical or biological process, such as denitrification of nitrates. Another option known in the art for measuring the concentration of an ionic compound dissolved in a porous medium solution is to use in situ measurement systems. These in situ measurement systems can include for instance a porous cup that includes a measuring cavity and into which the porous medium solution to be measured can diffuse. However, these systems also require a substantial length of time, i.e. up to days, to reach an equilibrium between ionic concentrations of the ionic compounds dissolved in the porous medium solution contained in the surrounding soil and the soil solution being measured inside the system and therefore, also result in delayed information instead of providing real time data.

The real-time and continuous knowledge of ionic concentrations in a porous medium solution can be used for instance as input variables in irrigation and fertigation control systems as well as in environmental monitoring to assess water quality. The real-time and continuous knowledge of ionic concentrations of specific mineral elements dissolved in a porous medium solution contained in a surrounding porous medium, such a soil for crop production, can also be used to evaluate the amount of these mineral elements leaching out of the root zone, for instance during high precipitation or during irrigation.

SUMMARY

In accordance with an aspect, there is provided an ionic concentration-measuring device for measuring an ionic concentration of at least one ionic compound in a porous medium solution contained in a porous medium. The device comprises a sensing portion including a permeable material body defining a measuring cavity therein and being insertable in the porous medium to allow the porous medium solution to diffuse into the measuring cavity through the permeable material body. The sensing portion includes at least one of: the permeable material body having an outside width smaller than about 8 mm and the measuring cavity having an inside width smaller than about 5 mm; the permeable material body having an external surface of less than about 1300 $mm^2$; the measuring cavity having a volume less than about 400 $mm^3$; and the permeable material body having a ratio between a volume of the measuring cavity and an external surface of the permeable material body (ratio volume cavity/external surface) of less than about 0.7 mm. The device also comprises a light source configured to generate illumination light to illuminate the porous medium solution contained inside the measuring cavity, and a light sensor configured to detect a resulting light emanating from the porous medium solution contained inside the measuring cavity upon illumination of the porous medium solution by the illumination light, the resulting light having at least one spectral characteristic indicative of the ionic concentration of the at least one ionic compound in the porous medium solution.

In some embodiments, the outside width of the permeable material body is between about 8 mm and about 6 mm, and the inside width of the measuring cavity is between about 3 mm and about 5 mm.

In some embodiments, the outside width of the permeable material body is smaller than about 6 mm and the inside width of the measuring cavity is smaller than about 3 mm.

In some embodiments, the inside width of the measuring cavity is smaller than about 2 mm.

In some embodiments, the external surface of the permeable material body is less than about 700 $mm^2$.

In some embodiments, the external surface of the permeable material body is between about 200 $mm^2$ and about 700 $mm^2$.

In some embodiments, the external surface of the permeable material body is less than about 200 $mm^2$.

In some embodiments, the volume of the measuring cavity is between about 400 $mm^3$ and about 200 $mm^3$.

In some embodiments, the volume of the measuring cavity is between about 200 $mm^3$ and about 100 $mm^3$.

In some embodiments, the volume of the measuring cavity is less than about 100 $mm^3$.

In some embodiments, the ratio volume cavity/external surface of the permeable material body is between about 0.7 mm and about 0.3 mm.

In some embodiments, the ratio volume cavity/external surface of the permeable material body is less than about 0.3 mm.

In some embodiments, the ionic concentration-measuring device further comprises a housing coupled to the sensing portion and at least partially insertable in the porous medium, the housing containing at least one of the light source, the light sensor, and a real-time data transmitter.

In some embodiments, the ionic concentration-measuring further comprises an optical probe mounted to the housing with the light sensor and the light source being contained in the optical probe.

In some embodiments, the light source is mounted to the permeable material body to illuminate the porous medium solution contained inside the measuring cavity.

In some embodiments, the light sensor is mounted to the permeable material body.

In some embodiments, the ionic concentration-measuring device further comprises at least one illumination light transmitter operatively connected to the light source to direct the illumination light towards the porous medium solution contained inside the measuring cavity for illuminating same.

In some embodiments, the ionic concentration-measuring device further comprises at least one resulting light transmitter operatively connected to the light sensor to allow the light sensor to detect the resulting light emanating from the porous medium solution contained inside the measuring cavity.

In some embodiments, the ionic concentration-measuring device further comprises at least one illumination light transmitter operatively connected to the light source to direct the illumination light towards the porous medium solution contained inside the measuring cavity for illuminating same; and at least one resulting light transmitter operatively connected to the light sensor to allow the light sensor to detect the resulting light emanating from the porous medium solution contained inside the measuring cavity.

In some embodiments, the at least one illumination light transmitter and/or the at least one resulting light transmitter has a distal end located inside the measuring cavity.

In some embodiments, the at least one illumination light transmitter and/or the at least one resulting light transmitter extends laterally along at least a section of the sensing portion and is mounted thereon.

In some embodiments, the at least one illumination Hight transmitter and/or the at least one resulting light transmitter comprises an optical fiber or an electric data transmitter.

In some embodiments, the ionic concentration-measuring device further comprises a reflector positioned inside the measuring cavity to reflect at least one of the illumination light and the resulting light to be detected and direct same to the light sensor.

In some embodiments, the light source emits in a visible, infrared, or ultraviolet range of the light spectrum to illuminate the porous medium solution contained inside the measuring cavity and the resulting light is unabsorbed light resulting from at least one of reflection, transmission, transmittance, interference and scattering.

In some embodiments, the light source emits an excitation light to induce at least one of fluorescence, phosphorescence luminescence, photoluminescence and chemiluminescence of the porous medium solution contained in the measuring cavity and the resulting light is emanating from at least one of fluorescence, phosphorescence luminescence, photoluminescence and chemiluminescence.

In some embodiments, the light source is capable of emitting at wavelengths allowing disinfection of the porous medium solution.

In some embodiments, the light sensor comprises a spectrophotometer including a photodetector and a filter.

In some embodiments, the light sensor comprises at least one of a filter, a narrow interference filter and an optical sensor for collecting, guiding, transforming, or affecting the illumination light and/or the resulting light.

In some embodiments, the optical sensor includes a bandpass filter, a lens, or an optical fiber.

In some embodiments, the light sensor comprises a plurality of light sensors, each one of the plurality of light sensors having a respective spectral responsivity.

In some embodiments, the light sensor is configured to convert the resulting light to an electrical signal to be processed by a processor, the electrical signal being indicative of and convertible into an ionic concentration.

In accordance with another aspect, there is provided a method for measuring in situ an ionic concentration of at least one ionic compound in a porous medium solution contained in a porous medium. The method comprises the steps of: inserting, in the porous medium, a sensing portion including a permeable material body defining a measuring cavity therein and wherein the sensing portion includes at least one of: the permeable material body having an outside width smaller than about 8 mm and the measuring cavity having an inside width smaller than about 5 mm; the permeable material body having an external surface of less than about 1300 mm$^2$; the measuring cavity having a volume less than about 400 mm$^3$; and the permeable material body having a ratio between a volume of the measuring cavity and an external surface of the permeable material body (ratio volume cavity/external surface) of less than about 0.7 mm; allowing the porous medium solution to naturally diffuse through the permeable material body towards and inside the measuring cavity; illuminating the porous medium solution contained inside the measuring cavity with illumination light; detecting a resulting light emanating from the porous medium solution contained inside the measuring cavity upon illumination of the porous medium solution by the illumination light; and determining the ionic concentration of the at least one ionic compound using at least one spectral characteristic of the resulting light.

In some embodiments, illuminating the porous medium solution contained inside the measuring cavity comprises generating illumination light using a light source.

In some embodiments, generating illumination light comprises emitting light in the UV region, IR region or NIR region of the light spectrum.

In some embodiments, generating illumination light comprises emitting excitation light to induce to induce at least one of fluorescence, phosphorescence luminescence, photoluminescence and chemiluminescence of the porous medium solution contained in the measuring cavity.

In some embodiments, generating illumination light using the light source comprises operatively connecting at least one illumination light transmitter to the light source to direct the illumination light towards the porous medium solution.

In some embodiments, detecting the resulting light is performed using a light sensor.

In some embodiments, detecting the resulting light further comprises reflecting the illumination light on a reflector positioned inside the measuring cavity to direct the resulting light towards the light sensor.

In some embodiments, detecting the resulting light comprises operatively connecting at least one resulting light transmitter to the light sensor to detect the resulting light emanating from the porous medium solution contained inside the measuring cavity.

In some embodiments, the method further comprises processing the resulting light to obtain a processed resulting light.

In some embodiments, the processed resulting light is obtained by filtering the resulting light with an interferential filter.

In some embodiments, the interferential filter comprises a bandpass filter centered on a wavelength or a wavelength range to be monitored.

In some embodiments, detecting the resulting light comprises converting the resulting light into an electrical signal.

In accordance with another aspect, there is provided an ionic concentration-measuring device for measuring in situ an ionic concentration of at least one ionic compound in a porous medium solution contained in a porous medium. The device includes a sensing portion, a light source and a light sensor. The sensing portion includes a porous material body defining a measuring cavity therein and being insertable in the porous medium to allow the porous medium solution to diffuse into the measuring cavity through the porous material body. The porous material body has an outside width smaller than about 8 mm and the measuring cavity has an inside width smaller than about 5 mm. The light source is configured to generate illumination light. The illumination light illuminates the porous medium solution inside the measuring cavity. The light sensor is in optical communication with the porous medium solution inside the measuring cavity to detect, as unabsorbed light, at least a portion of the illumination light which has not been absorbed by the porous medium solution. At least one spectral characteristic of the detected unabsorbed light signal is indicative of the ionic concentration of the at least one ionic compound in the porous medium solution.

In some embodiments, the ionic concentration-measuring device includes at least one light transmitter in optical communication with the light source to direct the illumination light towards the porous medium solution and has a distal end located in the measuring cavity for illuminating the same.

In some embodiments, the light sensor includes a spectrophotometer.

In some embodiments, the light sensor is mounted to the porous material body.

In some embodiments, the light sensor is located inside the measuring cavity.

In some embodiments, the ionic concentration-measuring also includes a housing coupled to the sensing portion and at least partially insertable in the porous medium therewith. The housing contains at least one of the light source, the light sensor, and a real-time data transmitter.

In some embodiments, the ionic concentration-measuring device also includes an absorbed light transmitter mounted to the porous material body, extending outwardly thereof. The absorbed light transmitter is operatively connected to the light sensor.

In accordance with another aspect, there is provided a method for measuring in situ an ionic concentration of at least one ionic compound in a porous medium solution contained in a porous medium. The method includes the steps of: inserting in the porous medium a sensing portion including a porous material body defining a measuring cavity therein and having an outside width smaller than about 8 mm and the measuring caving having an inside width smaller than about 5 mm; allowing the porous medium solution to diffuse through the porous material body towards and inside the measuring cavity; illuminating the porous medium solution inside the measuring cavity with illumination light; collecting and detecting, as unabsorbed light, at least a portion of the illumination light which has not been absorbed by the porous medium inside the measuring cavity; and determining the ionic concentration of the at least one ionic compound based on at least one spectral characteristic of the unabsorbed light.

DETAILED DESCRIPTION

Figure 1:
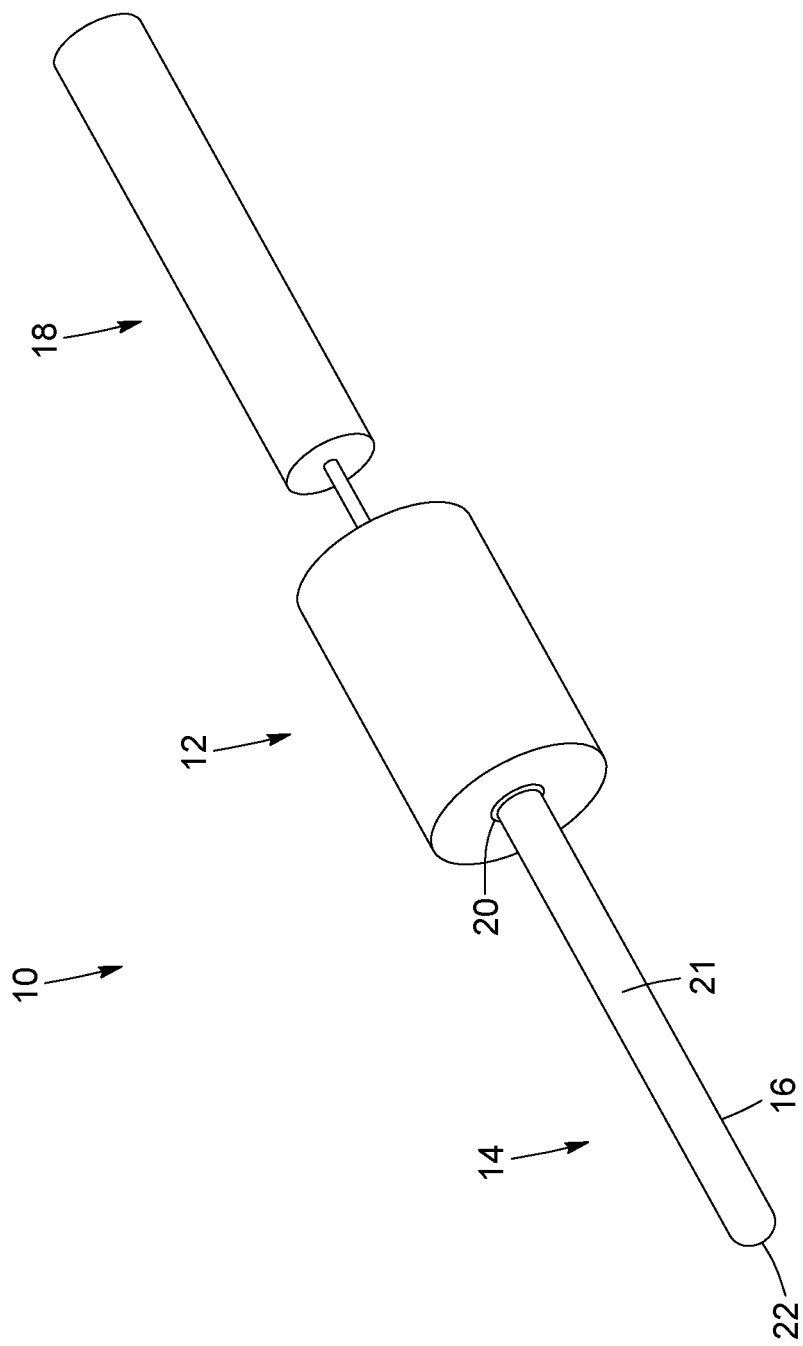
FIG. 1 is a schematic side perspective view of an ionic concentration-measuring device in accordance with an embodiment.

In the following description, there are described various embodiments related to an ionic concentration-measuring device for measuring in situ an ionic concentration of an ionic compound in a porous medium solution, such as a soil solution, contained in a surrounding porous medium. There are also described various embodiments related to a method for measuring in situ an ionic concentration of an ionic compound in a porous medium solution contained in a surrounding porous medium. It will be noted that in the drawings, the same numerical references refer to similar elements.

Although the embodiments of the ionic concentration-measuring device and corresponding parts thereof consist of certain geometrical configurations as explained and illustrated herein, not all of these components and geometries are essential and thus should not be taken in their restrictive sense. It is to be understood, as also apparent to a person skilled in the art, that other suitable components and cooperation thereinbetween, as well as other suitable geometrical configurations, may be used for the ionic concentration-measuring device, as will be briefly explained herein and as can be easily inferred herefrom by a person skilled in the art.

Moreover, it will be appreciated that positional descriptions such as "above", "lower", "upper", "below", "forward", "rearward" "left", "right" and the like should, unless otherwise indicated, be taken in the context of the figures and correspond to the position and orientation of the ionic concentration-measuring device and corresponding parts when inserted in the porous medium, with the "upper" corresponding to a portion closer to the exposed surface of the porous medium and the "lower" corresponding to a portion opposed to the upper portion. Positional descriptions should not be considered limiting.

In the present disclosure, the terms "light" and "optical" are meant to refer to electromagnetic radiation in any appropriate region of the electromagnetic spectrum. More particularly, the terms "light" and "optical" are not limited to visible light, but can also include invisible light, for example ultraviolet light or infrared light. By way of example, in some implementations, the terms "light" and "optical" may encompass an electromagnetic radiation having a wavelength ranging from about 210 to 300 nm. More particularly, although some implementations of the present techniques can be useful in ultraviolet applications, other embodiments can additionally or alternatively operate in other regions of the electromagnetic spectrum, for example in the millimeter, terahertz, visible and near-infrared and/or infrared regions.

In the present disclosure, the expression "real-time data" refers to data continuously collected by the ionic concentration-measuring device, once the equilibrium conditions are met. More specifically, the term "equilibrium" used herein refers to an equilibrium between the ionic concentration of the porous medium solution contained in the measuring cavity and the one contained in the surrounding porous medium. As such, the "real-time data" refers to information and/or results that are continuously available for processing, recording and analysis, after their acquisition by the ionic concentration-measuring device. In some context, the expression "real-time data" refers to information that is representative of the concentration of that ionic compound in the surrounding porous medium (at equilibrium). It is to be noted that the expression "real-time data acquisition", or the like, can refer, in some context, to "near real-time acquisition".

The terms "connected", "coupled", "operatively connected", "communication", and variants and derivatives thereof, refer to any connection or coupling, either direct or indirect, between two or more elements. The connection or coupling between the elements may be mechanical, physical, optical, operational, electrical or a combination thereof.

The expressions "illumination light" and "resulting light" used throughout the description are defined as follows:
1. "Illumination light" refers to light which is directly or indirectly (e.g., after a passage through an optical component) sent towards the sample under investigation (e.g., an ionic compound contained in a porous medium solution). The illumination light will sometimes be referred as an "excitation light", for example in the context where the sample has a ground (i.e., nonexcited) state and at least one excited state. In this context, the illumination light allows exciting the sample from its ground state to one of its excited state(s). The term "excitation" as used herein thus refers to an elevation from a lower energy level to a higher energy level, the elevation being attributable to the illumination (i.e., the excitation light) light.
2. "Resulting light" refers to light emanating from the sample (e.g., the ionic compound). The resulting light encompasses a broad variety of types of light emission, and includes reemitted light. For example, the resulting light can refer to light that has not been absorbed by the sample, light transmitted through the sample, or light scattered by the sample. The resulting light can also be the result of various physical processes, such as and without being limitative: luminescence, photoluminescence, fluorescence, phosphorescence, and the like. Hence, from a general point of view, the resulting light is the light emanating from the sample after the interaction between the illumination light and the sample (i.e., the ionic compound contained in the porous medium solution). In the context of the current description, the resulting light is sometimes referred to as "unabsorbed light".

In general terms, the present disclosure concerns an ionic concentration-measuring device for measuring in situ an ionic concentration of at least one ionic compound, and more particularly, an ionic compound dissolved in a solution contained in a surrounding porous medium.

For instance, and without being limitative, the porous medium can include earthen soil or greenhouse soil. The porous medium can be of different nature and comprise different components in various proportions. The porous medium can be a soil for crop production, which can comprise for instance and without being limitative, sand, peat, loam, silt, clay, and the like, each in various proportions. The porous medium can also be a porous medium comprising organic and inorganic compounds in various proportions, and be used for instance and without being limitative as a growing medium for greenhouses, nursery production, landscaping and urban agriculture. Soils other than those for crop production are also within the scope of the present description. The porous medium can also contain a variable content of a water-based solution, for example and without being limitative a solution eventually leaching out of the soil to form the porous medium solution (or soil solution), or the porous medium solution which will eventually diffuse through the permeable material body, as it will be described in greater detail in a subsequent section.

The ionic concentration-measuring device described herein for in situ measurements of ionic concentrations, i.e. for measurements performed directly on site, can allow for the determination of ionic concentrations in the porous medium solution in real-time, once the appropriate equilibrium is reached, or at least in a substantially continuous manner.

In some implementations, the determination of the ionic concentrations using the ionic concentration-measuring device as described herein is autonomous, i.e., does not require human intervention and/or the generation of an artificial flux of porous medium solution into the measuring cavity of the permeable material body. Hence, the determination of the ionic concentrations is made possible at least in part because of the natural passive diffusion of the porous medium solution through the permeable material body and into the measuring cavity. In some implementations, the determination of the ionic concentrations is at least partially an automatic operation, and so could be compatible with a method comprising automated step(s).

In some embodiments described herein, the ionic concentration-measuring device generally comprises a housing, a sensing portion, a light source, and a light sensor. The sensing portion includes a permeable material (also sometimes referred to as "porous material") body defining a measuring cavity. More particularly, in an embodiment, the permeable material body is in fluid communication with the measuring cavity (also sometimes referred to as the "measurement cavity"). In another embodiment, the measuring cavity extends longitudinally along the permeable material body. When the sensing portion is inserted in a porous medium, the measuring cavity can extend vertically or horizontally, as will be described in more detail below.

The sensing portion is insertable in the porous medium to allow a sample of the porous medium solution contained in the surrounding porous medium to passively diffuse into the measuring cavity through the permeable material body, i.e. the movement of ions across permeable material body without need of energy input, human or mechanical intervention. To obtain substantially a real-time equilibrium between the ionic concentration of the porous medium solution contained in the measuring cavity and the one contained in the surrounding porous medium, both the permeable material body and its measuring cavity are relatively small.

The miniaturisation of the measuring cavity helps reducing the time required to reach the ionic equilibration between the porous medium solution contained in the surrounding porous medium and the porous medium solution contained within the measuring cavity, and can allow, under the proper conditions, to perform real-time monitoring (or in a relatively short amount of time) to determine the concentration of the ionic compound. The miniaturisation contributes to providing a concentration value of the ionic compound to be measured closely representing that of the porous medium solution contained in the porous medium within a smaller time interval than the ionic concentration-measuring devices currently known in the art, for instance in the range of hours or even minutes. Such information can be useful for instance to optimize the fertilization management of crops by monitoring the porous medium nutrients and/or to characterize porous medium contaminants accurately for environmental purposes.

In the context of the present description, the miniaturisation of the permeable material body can be expressed using various dimensions, or ratios. For instance, the dimensions of the permeable material body can be expressed according to the diameter of the measuring cavity, which can also be referred to as an inside width of the measuring cavity, and according to the diameter of the permeable material body, which can also be referred to as an outside width of the permeable material body. In some implementations, the permeable material body has an outside width smaller than about 8 mm, and the measuring cavity has an inside width smaller than about 5 mm. In other implementations, the permeable material body has an outside width smaller than about 6 mm and the measuring cavity has an inside width smaller than about 3 mm. In yet other implementations, the measuring cavity has an inside width smaller than about 2 mm. Another dimension that can be used to characterize the sensing portion is the volume of the internal cavity of the permeable material body. For instance, in the case of a measuring cavity having a tubular configuration, it can be useful to express the dimension of the measuring cavity as a volume, for example to take into consideration the length of the measuring cavity. In some implementations, the volume of the cavity is less than about 400 $mm^3$. In other implementations, the volume of the cavity is less than about is less than about 200 $mm^3$. In still other implementations, the volume of the cavity is less than about 100 $mm^3$. In yet other implementations, the volume of the cavity is less than about 20 $mm^3$. The dimension of the permeable material body can also be expressed with regard to its external surface. In some implementations, the external surface of the permeable material body is less than 1300 $mm^2$. In other implementations, the external surface is less than 700 $mm^2$. In yet other implementations, the external surface is between about 200 $mm^2$ and about 700 $mm^2$. In still other implementations, the external surface of the permeable material body is less than about 200 $mm^2$. The dimension of the permeable material body can also be expressed as a ratio of the volume of the measuring cavity relative to the external surface of the permeable material body. In some implementations, the ratio [volume of measuring cavity/external surface of permeable material body] is less than about 0.7 mm. In other implementations, the ratio [volume of measuring cavity/external surface of permeable material body] is less than about 0.3 mm. In yet other implementations, the ratio [volume of measuring cavity/external surface of permeable material body] is less than about 0.1 mm. In other implementations, the ratio [volume of measuring cavity/external surface of permeable material body] is less than about 0.08 mm. In some other implementations, the outside surface of the permeable material body is less than about 1300 $mm^2$ and the measuring cavity has an inside volume of less than 200 $mm^3$. It is to be understood that the sensing portion can have various shapes such as tubular, spherical, or any suitable shape according to the dimensions described above that allows for the diffusion of the porous medium solution into the measuring cavity. For instance, a spherical permeable material body can have an inside diameter of 2 mm, an external surface of 80 $mm^2$, a volume cavity of 4 $mm^3$, and a ratio [volume of measuring cavity/external surface of permeable material body] of approximately 0.05 mm.

Of course, the abovementioned dimensions can vary, depending on the targeted applications, and are presented for example purpose only. In implementations where the perimeter of the permeable material body is irregular, for instance when the permeable material body is neither tubular nor spherical, a mean width can be used to express width dimension(s) of the permeable material body.

In one implementation, for example when the outside width of the permeable material body is about 8 mm and the inside width of the permeable material body is about 5 mm, the permeable material body has an outside surface smaller than about 650 $mm^2$, and is in fluid contact with the measuring cavity, which has an inside volume of less than 400 $mm^3$. In this implementation, the outside length (i.e., the length of the permeable material body) can be, for example, be about 25 mm and the inside length (i.e., the length of the measuring cavity) can be about 20 mm.

In another implementation, the outside width is about 6 mm and the outside width is about 3 mm and the inside width is about 3 mm. In this context, the outside surface of the permeable material body is smaller than about 200 mm$^2$ and the inside volume is about 15 mm$^3$. In this implementation, the outside length (i.e., the length of the permeable material body) can be about 10 mm and the inside length (i.e., the length of the measuring cavity) can be about 2 mm.

The light source is configured to generate illumination light to illuminate the porous medium solution contained inside the measuring cavity. In an embodiment, the light source can be mounted to the permeable material body and illuminate directly the porous medium solution contained therein. In another embodiment, the ionic concentration-measuring device can include an illumination light transmitter channel in optical communication with the light source and have a distal end inserted into the measuring cavity or in light communication with the measuring cavity to illuminate the porous medium solution contained therein.

The light sensor is configured to detect a resulting light emanating from the porous medium solution inside the measuring cavity upon illumination of the porous medium solution by the illumination light. The resulting light has at least one optical property or at least one spectral characteristic (e.g., optical emission) indicative of the ionic concentration of the at least one ionic compound in the porous medium solution. As such, the light sensor can be said to be in optical communication with the porous medium solution inside the measuring cavity, because the light sensor receives (i.e., detect) light emanating from the porous medium solution. As previously mentioned, the resulting light can encompass a broad variety of types of light emission and/or light reemission. The light sensor can thus measure, for example and without being limitative: unabsorbed light which could result from physical mechanisms such as reflection, transmission, transmittance, interference, or scattering, and/or light emitted through physical and/or chemical mechanisms, such as luminescence, photoluminescence, fluorescence, phosphorescence, and the like.

For example, in one embodiment, the light sensor is in optical communication with the porous medium solution inside the measuring cavity to detect, as unabsorbed light, at least a portion of the illumination light which has not been absorbed by the porous medium solution. In another embodiment, the transmittance properties are measured by detecting the portion of the illumination light that has not been absorbed by the porous medium solution to determine the absorbance of the ionic compound.

In some implementations, the porous medium solution inside the measuring cavity is excited by means of an excitation light emitted by the light source (i.e., the illumination light), which may pass through a filter to induce fluorescence, phosphorescence or chemiluminescence of the porous medium solution contained in the measuring cavity. The ionic concentration of the at least one ionic compound is then determined through the light sensor, based on the emission spectra of the light emitted by (i.e., emanating from) the porous medium solution as a result of the excitation.

In some embodiments, the light sensor comprises a photodetector and a filter, acting together as a spectrophotometer and, more particularly, a miniature spectrophotometer (hereinafter referred to as a "mini-spectrophotometer" or simply as the "spectrophotometer"). In some embodiments, the light sensor includes a filter to select or isolate a specific range of wavelengths, before the detection of the resulting light.

The light sensor can be mounted to the permeable material body. For instance, it can be positioned at least at one end of the permeable material body and/or it can be located inside the measuring cavity. The light sensor can be configured to generate an electrical signal that can be converted to an ionic concentration by an appropriate calibration equation, as it will be described in greater detail below. It is to be noted that the appropriate calibration equation can be specific to one ionic compound or one class of ionic compound. It can be a phenomenological-based calibration equation, an empiric calibration equation, or a combination of both.

As it has been previously introduced, the ionic concentration of the at least one ionic compound in the porous medium solution is determined based on the at least one optical property or, alternatively on the at least one spectral characteristic of the detected resulting light collected by the light sensor. For example, and as it has been previously mentioned, the light sensor can be configured to detect (i.e., receive) the resulting light from the porous medium solution. The resulting light, as it can be emitted through various physical and/or chemical processes (e.g., absorption, transmission, transmittance, reflection, fluorescence, luminescence, and the like), can have different optical properties. For instance and without being limitative, the optical emission spectrum of the resulting light can include different regions of the electromagnetic spectrum (i.e., wavebands), such as: ultraviolet (UV), visible, infrared (IR), near infrared (NIR), or any other region(s) of the electromagnetic spectrum, depending, for example, on the nature of the ionic compound being characterized, but also on the interaction between the illumination light and the ionic compound present in the porous medium solution.

For measuring in situ an ionic concentration of at least one ionic compound in a porous medium solution contained in a porous medium using an embodiment of the above-described ionic concentration-measuring device, the sensing portion including a permeable material body is inserted in the porous medium to allow the porous medium solution contained in the surrounding porous medium to diffuse through the permeable material body towards and inside the measuring cavity. Then, the porous medium solution inside the measuring cavity is illuminated with illumination light emitted by the light source. The resulting light is collected and detected by the light sensor. The ionic concentration of the at least one ionic compound is determined based on at least one spectral characteristic of the resulting light.

The ionic concentration-measuring device can be operated in different modes. In some implementations, the ionic concentration-measuring device can allow measuring the concentration of the ionic compound in real-time. As mentioned above, the ionic concentration-measuring device can include a housing coupled to the sensing portion. The housing can be at least partially insertable in the porous medium together with the sensing portion. The housing can contain at least one of the light source, a light sensor, an optical filter, and a real-time data transmitter, as will be described in more detail below. The real-time data transmitter can be provided for transmitting the electrical signal data generated by the spectrophotometer, for instance to a local system or to web servers, for various analysis and uses, including the determination of the at least one ionic compound concentration based on the detected light (i.e., the resulting light).

In another implementation, the ionic concentration-measuring device can allow measuring the concentration of the ionic compound in deferred time. The housing can be at least partially insertable in the porous medium together with the sensing portion. The housing can contain at least one of the light source, at least one of the light sensor, an optical filter, and a data transmitter, as will be described in more detail below. The data transmitter can be provided for transmitting the electrical signal data generated by the spectrophotometer, for instance to a local system or to web servers, for conducting differed analysis, including the determination of the at least one ionic compound concentration based on the detected optical signal (i.e., the resulting light). It is to be noted that, in this implementation, the local system or the web servers can be provided with a memory for collecting, stocking and saving data prior to their analysis, such that the data can be processed at a later time.

The ionic compound can comprise, for instance and without being limitative, nitrate ions, calcium ions, potassium ions, phosphate ions, ammonium ions or magnesium ions. In an embodiment, the ionic compound comprises nitrate ions.

In an embodiment, the light source emits in a selected range of the light spectrum (e.g., in the visible, IR or UV spectrum). An example of a light source emitting in a large range of the light spectrum can be for instance a deuterium or a xenon lamp. In other embodiments, depending on the ionic compound to be detected and/or the concentration of the ionic compound to be measured, the light source can be a light source such as, but not limited to, a light emitting diode (LED), emitting over a narrower spectral range. Alternatively, the light source could also be based on different lighting technologies such as, for example, solid-state lighting including lasers, organic LEDs (OLEDs), incandescent lighting, halogen lighting, fluorescent light, infrared heat emitters, and discharge lighting.

Having discussed the general context of the ionic concentration-measuring device, optional embodiments will be discussed further hereinbelow. The embodiments according to the following description are given for exemplification purposes only.

In accordance with a first aspect and with reference to FIGS. 1, 2, 3A and 3B, a first embodiment of an ionic concentration-measuring device 10 to measure ionic concentrations of at least one ionic compound dissolved in a porous medium solution is shown. As mentioned hereinabove, the porous medium solution refers for example to a water-based or aqueous solution present in the pores, or interstices, of the porous medium that eventually passively diffuses through the permeable material body to reach the measuring cavity. In some scenarios, the porous medium solution can contain water and variable concentrations (e.g., trace amounts) of dissolved compounds and suspended material, such as organic matter, minerals and various other elements typically found into the ground. The ionic concentration-measuring device 10 includes a housing 12, a sensing portion 14 mechanically coupled to the housing 12 and including a permeable material body 16, and a light sensor 18 mounted to the housing 12.

In the embodiment shown, the housing 12 and the permeable material body 16 are tubular. The housing 12 can be made of a corrosion resistant-material such as substantially rigid polymers or corrosion-resistant materials and alloys.

Figure 2:
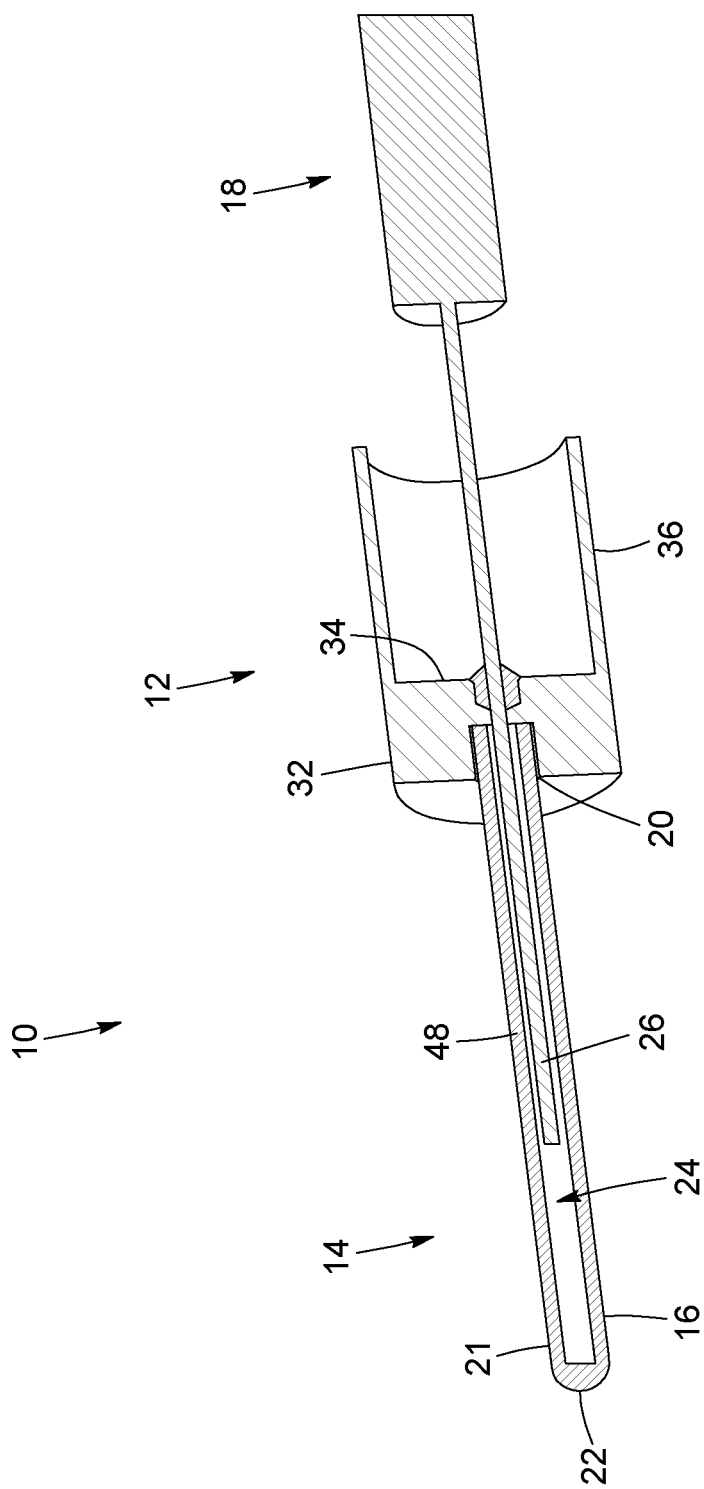
FIG. 2 is a schematic cross-sectional perspective view of the ionic concentration-measuring device shown in FIG. 1.

The permeable material body 16 (which can also be referred to as a porous material body) includes a proximal end 20, coupled to the housing 12, a distal end 22, opposed to the proximal end 20, and an outer surface 21. It is to be understood that other suitable shapes of the permeable material body 16 are also envisioned and are within the scope of the present description. Referring to FIGS. 2 and 3, the permeable material body 16 defines a measuring cavity 24 extending longitudinally along a central axis thereof. In the embodiment shown, the distal end 22 of the permeable material body 16 is a closed end, i.e. the measuring cavity 24 is closed at a lower end thereof, and is intended to be the first end inserted in the porous medium when the ionic concentration-measuring device 10 is in use. In some implementations, the proximal end 20 of the permeable material body 16 is an open end to allow insertion, in the measuring cavity 24, of a distal end of an illumination light transmitter or directly a light source and a distal end 26 of the light sensor 18 or a distal end of a resulting light transmitter. In the embodiment shown in FIGS. 1 to 3B, distal ends of the resulting and illumination light transmitters are inserted and located inside the measuring cavity 24.

The permeable material body 16 can be made of any suitable material that allows the passive diffusion of the porous medium solution therethrough. In some implementations, the permeable material body 16 comprises a porous material, for example and without being limitative ceramic, porous stainless-steel or other porous materials. It will be readily understood that other materials can be used, for example and without being limitative, plastics or polymers. The pores of the permeable material body 16 can have different sizes and shapes, which can be regular or irregular (i.e. have regular or irregular shape), and can be homogeneously or heterogeneously distributed, depending for instance on the material used.

In the embodiment shown in FIG. 3B, the light sensor 18 and the light source 17 are contained in an optical probe 31 mounted to the housing 12. The optical probe as used herein can refer to a single integrated device including a plurality of interconnected components allowing the light sensor 18 to carry out its function. Alternatively, the light sensor 18 can also be embodied by a plurality of interconnected devices.

The light sensor 18 is in optical communication with a resulting light transmitter, which can either be a light transmitter, such as an optical fiber, or an electric data transmitter, such as an electric connector, having a distal end located inside the measuring cavity 24. The light source 17 is also in optical communication with an illumination light transmitter, such as optical fiber, also having a distal end located inside the measuring cavity 24 to illuminate the porous medium solution contained therein.

The light sensor 18 can also include filter(s), narrow interference filter(s), optical sensor(s) including multiple bandpass filters, lenses, optical fibers and/or other optical components for collecting, guiding, transforming, or otherwise affecting the illumination light and/or the resulting light. In one example, the optical components aforementioned may be provided in a path of the light extending from the illumination light transmitter and the porous medium solution, and/or a path of the light extending from the porous medium solution and the resulting light transmitter, such that only light having the desired spectral contents reaches the porous medium solution and/or the light sensor 18. In other examples, different configurations can be used to extract spectral information from the illumination light and/or the resulting light, such as using a spectrometer or other spectrally resolved detector to convert the optical energy into analog or digital information.

In some implementations, the ionic concentration-measuring device 10 includes a plurality of light sensors 18. In such implementations, each one of the plurality of light sensors 18 can have different optical properties (e.g., spectral responsivity), and accordingly can be operated in different range(s) of wavelengths (e.g., complementary ranges of wavelengths).

The light sensor 18 can also be configured to convert the resulting light received by the light sensor 18 to an electrical signal to be processed by a processor, as will be explained in greater detail below.

Referring again to FIGS. 2, 3A and 3B, the housing 12 includes a permeable material body receiving section 32 having an internal surface 34 and a wall extending 36 away from the permeable material body receiving section 32 and defining a central cavity 38. The housing 12 also includes an outer lower surface 40 at a distal end of the permeable material body receiving section 32. In the illustrated embodiment, a sensing portion receiving cavity 42 is defined in the permeable material body receiving section 32 of the housing 12 and extends upwardly from the outer lower surface 40. The sensing portion receiving cavity 42 is sized and configured to receive the proximal end 20 of the permeable material body 16 therein.

In the embodiment shown, a transmitter channel 44 is also defined in the permeable material body receiving section 32 of the housing 12 and extends therethrough, up to the internal surface 34 of the permeable material body receiving section 32 from the sensing portion receiving cavity 42. More particularly, the transmitter channel 44 is open in both the central cavity 38 and the sensing portion receiving cavity 42 in a manner such that the illumination and resulting light transmitters can extend therethrough. In some implementations, the sensing portion receiving cavity 42 can contribute to stabilize the proximal end 20 of the permeable material body 16. To further stabilize the distal end 26 of the light sensor 18 and as shown in FIGS. 2 and 3, an adhesive 46 can be added to complete the filling of the transmitter channel 44. Thus, in the embodiment shown, the width of the sensing portion receiving cavity 42 is at least sufficient to receive the proximal end 20 of the permeable material body 16 therein and the width of the transmitter channel 44 is at least sufficient to contain the illumination and resulting light transmitters or the electrical connectors (if any) therein.

Figure 3A:
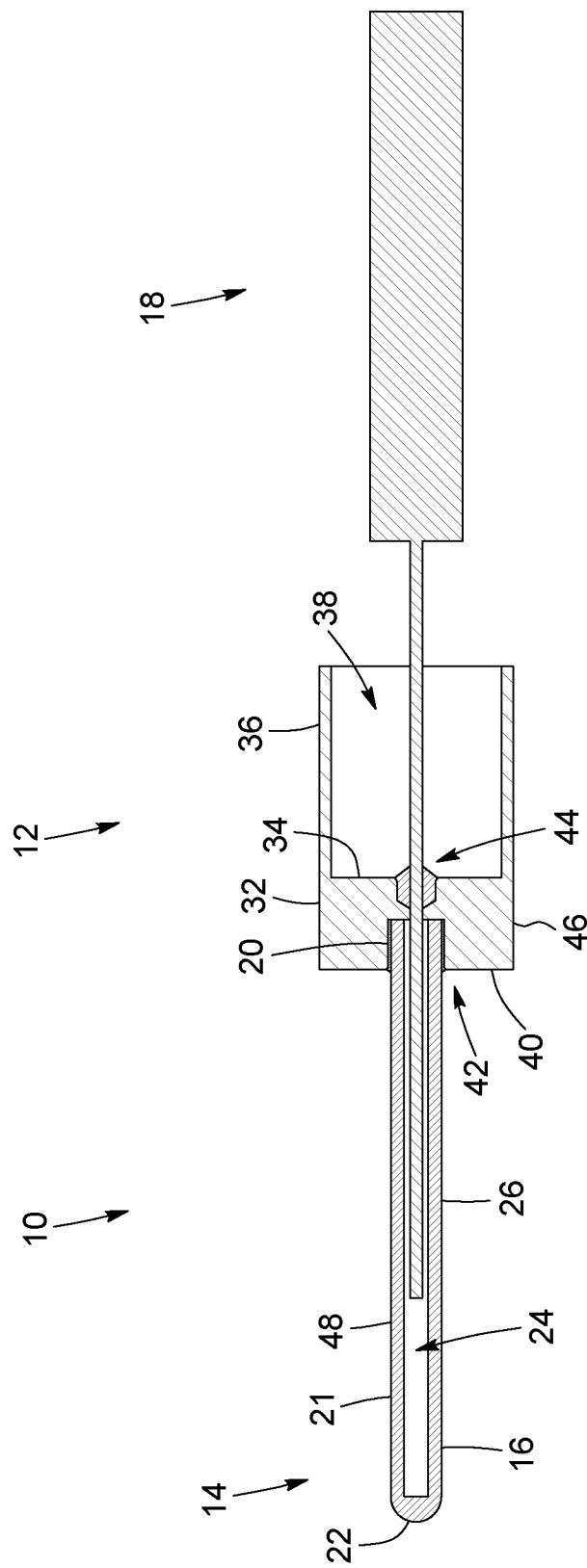
FIG. 3A is a schematic cross-sectional side elevation view of the ionic concentration-measuring device shown in FIG. 1.
Figure 3B:
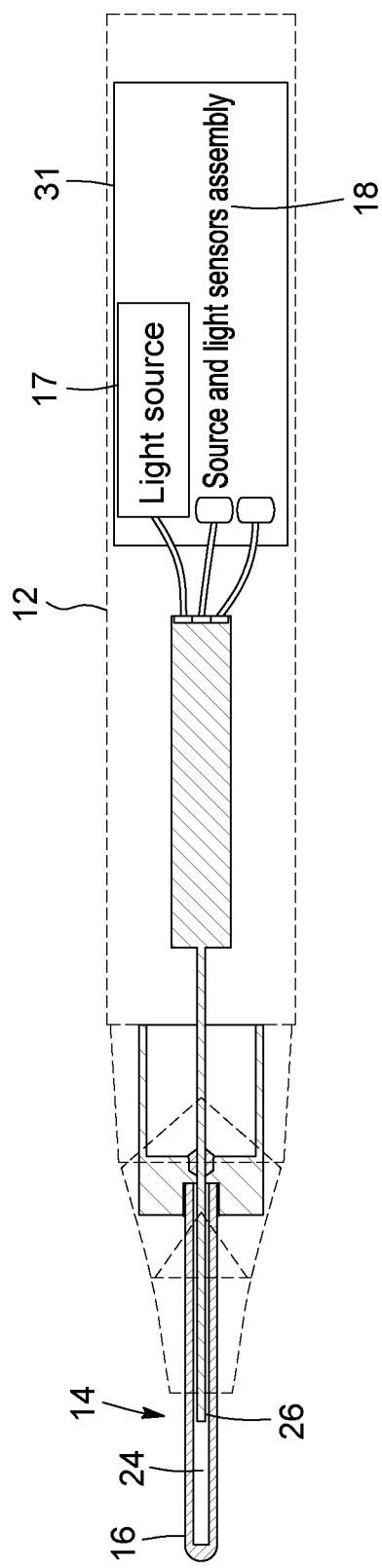
FIG. 3B is a schematic cross-sectional side elevation view of another embodiment of the ionic concentration-measuring device, wherein a light source and light sensor assembly are shown.

Still referring to FIGS. 2, 3A and 3B, in the embodiment shown, the measuring cavity 24 of the permeable material body 16 has a sufficient inside width to contain the distal end 26 of the light sensor 18 and the distal end of the resulting light transmitter or light sensor therein. In some embodiments, the inside width of the measuring cavity 24 can also be influenced by the strength that the permeable material body 16 is required to have in order to sustain a given force, for instance the force exerted on the outer surface 21 of the permeable material body 16 when the sensing portion 14 is inserted into the porous medium. Thus, the thickness of the walls 48 of the permeable material body 16 can be determined at least in part by the width of the distal end 26 of the light sensor 18 and/or the distal end of the light transmitter (s) being inserted into the measuring cavity 24 and their required strength.

As mentioned hereinabove, the miniaturisation of the ionic concentration-measuring device 10, and in particular of the permeable material body 16, can be expressed according to various dimensions. In some implementations, the measuring cavity 24 of the permeable material body 16 has an inside width smaller than about 5 mm and outside width of less than about 8 mm. In other implementations, the permeable material body has an outside width smaller than about 6 mm and the measuring cavity has an inside width smaller than about 3 mm. In yet other implementations, the measuring cavity has an inside width smaller than about 2 mm. Hence, in some implementations, the wall thickness of the housing 12 is at least about 3 mm. The gap defined between the distal ends of the light sensor 18 and the light transmitter and the inner wall of the permeable material body 16 can also be influenced by technical considerations related for instance to the formation of gas bubbles in the measuring cavity 24, which can impair the accuracy of the measures. This aspect will be discussed in more detail hereinbelow.

In some implementations, the permeable material body 16 has an external surface of less than 1300 $mm^2$. In other implementations, the permeable material body 16 has an external surface of less than 700 $mm^2$. In yet other implementations, the external surface of the permeable material body is between about 200 $mm^2$ and about 700 $mm^2$. In still other implementations, the external surface of the permeable material body is less than about 200 $mm^2$.

In some implementations, the volume of the measuring cavity is between about 400 $mm^3$ and about 200 $mm^3$. In other implementations, the volume of the measuring cavity is between about 200 $mm^3$ and about 100 $mm^3$. In yet other implementations the volume of the measuring cavity is less than about 100 $mm^3$. In yet other implementations the volume of the measuring cavity is less than about 20 $mm^3$.

In some implementations, the ratio [volume cavity/external surface] of the permeable material body is between about 0.7 mm and about 0.3 mm. In other implementations, ratio [volume cavity/external surface of the permeable material body] is less than about 0.3 mm.

The optical probe (or the ionic concentration-measuring device 110) further includes a data treatment unit, which can include the processor described hereinabove and/or related electrical circuitry. The processor is generally configured to process an electrical signal generated by the light sensor 18 to an ionic concentration using, for example, a calibration equation and/or an appropriate theoretical or empirical model(s). The processing of the electrical signal generally depends upon a device calibration and/or a reference signal. It is to be noted that the calibration equation may vary depending on the nature and the concentration of the ionic compound under investigation.

It is appreciated that the electrical signal can be filtered or processed otherwise before being processed (i.e., "converted") into ionic concentrations. Furthermore, either the housing 12 or the optical probe mounted to the housing 12 can include a data transmitter, such as a real-time or a near real-time data transmitter. In an embodiment, the data transmitter is a wireless data transmitter in data communication with a computer system. The electrical signal data and/or the ionic concentration can be sent to the computer system through the data transmitter. It is to be noted that the processor can be provided with the computer system, and that the processing of the resulting light or associated electrical signal can at least be partially carried out by the processor provided with the computer system.

In some implementations, once detected by the light sensor 18, the resulting light can be subsequently processed according to methods known in the art to obtain a processed resulting light. For instance, the resulting light may be filtered by an interferential filter or the like, such as a bandpass filter centered on a wavelength or a wavelength range to be monitored, and detected by a photodiode or similar device to convert the light to an electrical signal. In some variants, the entire spectral content of the collected light may be detected by the photodiode and the resulting light intensity value monitored.

In some embodiments, the processed resulting light can be displayed and monitored over a period of time. Depending on the operating mode of the ionic concentration-measuring device, the displaying and the monitoring can be carried out in real-time, near real-time or in differed time, as previously described.

Figure 4B:
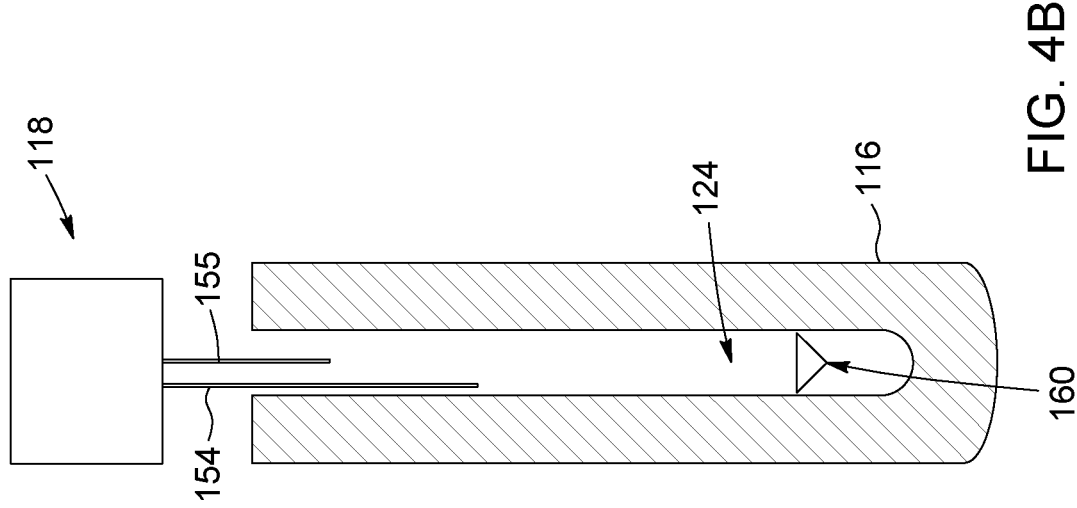
FIG. 4B is an enlarged schematic cross-sectional front elevation view of a portion of the ionic concentration-measuring device shown in FIG. 4A, showing a light assembly, an illumination light transmitter and a resulting light transmitter (i.e., a "light sensor"), wherein respective distal ends of the illumination light transmitter and the resulting light transmitter are inserted within a measuring cavity of the permeable material body.
Figure 4A:
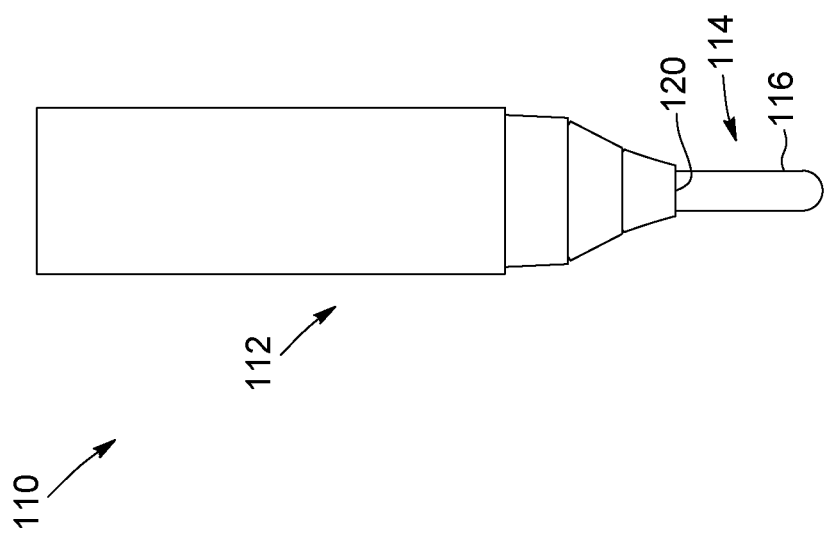
FIG. 4A is a schematic front elevation view of an ionic concentration-measuring device in accordance with an embodiment, wherein the ionic concentration-measuring device includes a housing coupled to a sensing portion that includes a permeable material body.

Referring now to FIGS. 4A and 4B, an alternative embodiment of an ionic concentration-measuring device to measure ionic concentrations of at least one ionic compound dissolved in a porous medium solution is shown wherein the features of the ionic concentration-measuring device are numbered with reference numerals in the 100 series which correspond to the reference numerals of the previous embodiment. As shown in FIG. 4A, in this alternative embodiment, the ionic concentration-measuring device 110 includes a housing 112, a sensing portion 114 that includes a permeable material body 116, and a light assembly 118. The light assembly 118 contains a light source (not shown) and a light sensor (not shown), and is enclosed in the housing 112. In this embodiment, the housing 112 is sized to house at least the light assembly 118 including the light source which, as shown in FIG. 4B, is in optical communication with an illumination light transmitter 154, such as at least one optical fiber and a resulting light transmitter 155 in optical communication with the light sensor. In the embodiment shown, the light sensor is contained in the light assembly 118. However, in an alternative embodiment, the light sensor can be either contained in the measuring cavity 124, close to a lower end thereof or adjacent to a distal end of the illumination light transmitter. If the light sensor is contained in the housing 112 or in the measuring cavity 124 and adjacent to the illumination light transmitter 154, the light assembly 118 also includes a reflector 160 mounted in the measuring cavity 124, close to the lower end thereof, to reflect resulting light, such as unabsorbed light, towards the light sensor, optionally through the resulting light transmitter 155. Similar considerations relative to the dimensions of the housing 112 and the measuring cavity 124 as the ones described hereinabove in reference to the embodiment shown in FIGS. 1 to 3 are also applicable to the embodiment shown in FIGS. 4A and 4B.

Figure 5A:
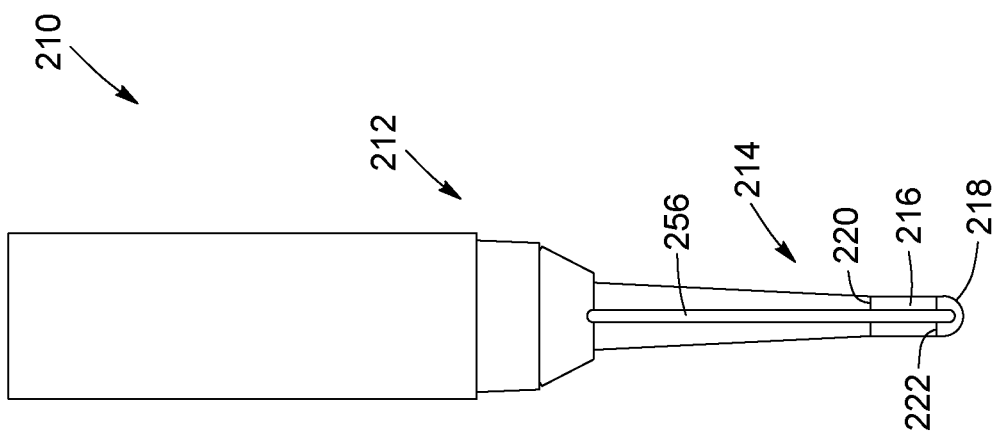
FIG. 5A is a schematic front elevation view of an ionic concentration-measuring device in accordance with another embodiment, wherein the ionic concentration-measuring device includes a housing coupled to a sensing portion including a permeable material body and a light sensor mounted at a distal end thereof.
Figure 5B:
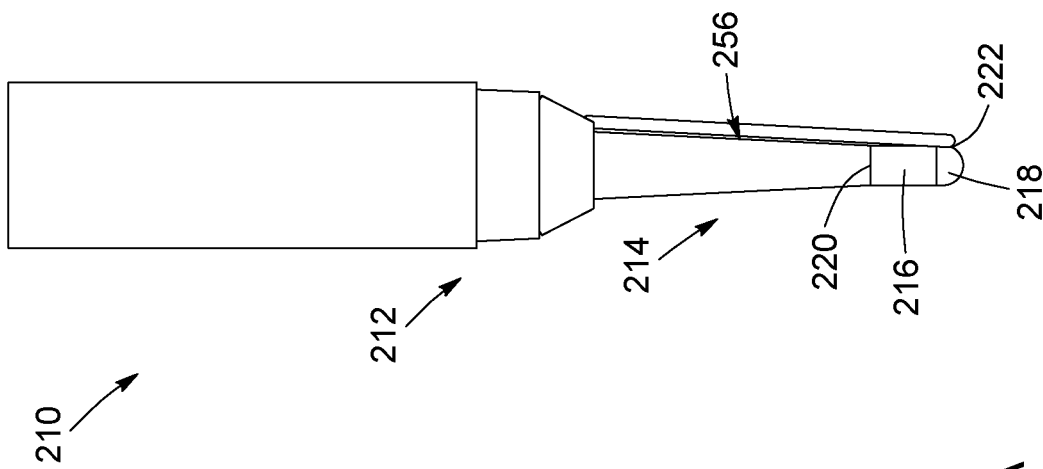
FIG. 5B is a schematic side elevation view of the ionic concentration-measuring device shown in FIG. 5A.

Referring now to FIGS. 5A and 5B, an alternative embodiment of an ionic concentration-measuring device to measure ionic concentrations of at least one ionic compound dissolved in a porous medium solution is shown wherein the features of the ionic concentration-measuring device are numbered with reference numerals in the 200 series which correspond to the reference numerals of the previous embodiments.

In this alternative embodiment, the ionic concentration-measuring device 210 includes a housing 212, a sensing portion 214 that includes a permeable material body 216 defining a vertically extending measuring cavity (not shown) therein, a light source (not shown) configured to illuminate the porous medium solution contained in the measuring cavity, and a light sensor 218. In this embodiment, the light source is external to the housing 212 and is in optical communication with an illumination light transmitter, such as an optical fiber, as will be explained in more detail hereinbelow. In an alternative embodiment, the light source can also be mounted to the permeable material body 216. In the embodiment shown, the permeable material body 216 has a proximal end 220 coupled to the housing 212 and a distal end 222 opposed to the proximal end 220. The light sensor 218 is mounted to the distal end 222 of the permeable material body 216. The distal end 222 of the permeable material body 216 is an open end such that the light sensor 218 can be in optical communication with the porous medium solution contained in the measuring cavity and detect the resulting light such as at least the portion that has not been absorbed by the porous medium solution. In the embodiment shown, the ionic concentration-measuring device 210 includes a light transmitter 256 extending laterally along an outer wall of the sensing portion 214 and mounted thereon. The light transmitter 256 can be a resulting light transmitter or an illumination light transmitter. When the light transmitter 256 is an illumination light transmitter, the light transmitter 256 in optical communication with the light source is configured to illuminate the porous medium solution contained in the measuring cavity. In the embodiment where the light transmitter 256 is a resulting light transmitter, which can be for instance an optical fiber or an electric data transmitter, the light transmitter 256 is in optical communication with the light sensor 218 to allow the light sensor 218 to collect and detect the resulting light, such as the light that has not been absorbed by the porous medium solution, i.e. the unabsorbed light. For instance, the resulting light transmitter can be an electric data transmitter when the conversion of the resulting light into an electrical signal is performed in close proximity of the light sensor 218. It is to be understood by a person skilled in the art that when the light transmitter 256 is an illumination light transmitter, the resulting light transmitter can be contained in the housing 212 of the ionic concentration-measuring device 210, and vice versa. In some implementations, the light transmitter 256 can comprise a portion extending within the housing 212 and an end, opposed to the light sensor 218, connected to the light source if the light transmitter 256 is an illumination light transmitter, or connected for instance to a real-time data transmitter if the light transmitter 256 is a resulting light transmitter.

Figure 6B:
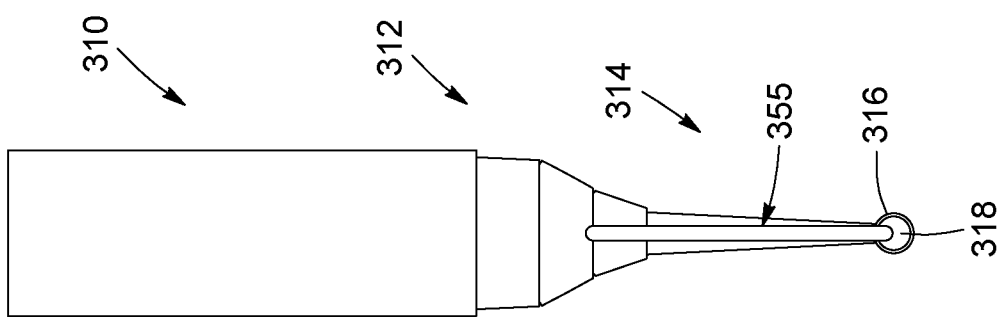
FIG. 6B is a schematic side elevation view of the ionic concentration-measuring device shown in FIG. 6A.
Figure 6A:
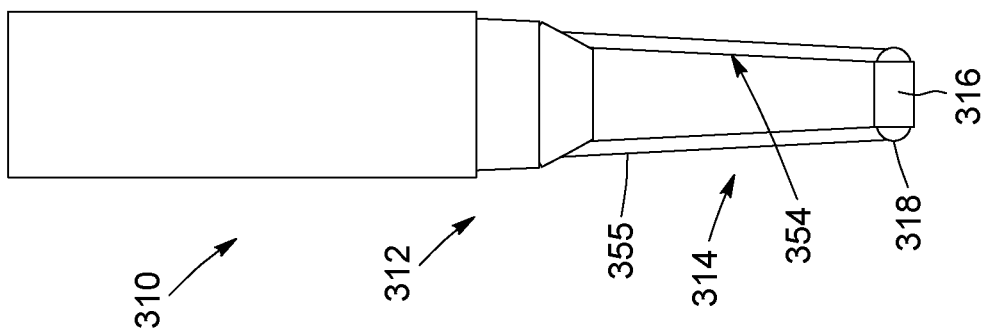
FIG. 6A is a schematic front elevation view of an ionic concentration-measuring device in accordance with another embodiment, wherein the ionic concentration-measuring device includes a housing coupled to a sensing portion including a permeable material body having two opposed ends, and a light sensor mounted to one of the opposed ends of the permeable material body.

Referring now to FIGS. 6A and 6B, an alternative embodiment of an ionic concentration-measuring device to measure ionic concentrations of at least one ionic compound dissolved in a porous medium solution is shown wherein the features of the ionic concentration-measuring device are numbered with reference numerals in the 300 series which correspond to the reference numerals of the previous embodiments. In this alternative embodiment, the ionic concentration-measuring device 310 includes a housing 312, a sensing portion 314 that includes a permeable material body 316 defining a horizontally extending measuring cavity therein, a light sensor 318, and a light source (not shown).

As described for FIGS. 5A and 5B, in this embodiment, the light source is external to the housing 312. In an alternative embodiment, the light source can also be mounted to the permeable material body 316. Thus, in this embodiment, the orientation of the permeable material body 316 and hence of the measuring cavity defined therein is different from the one shown in FIGS. 5A and 5B. In this embodiment, the permeable material body 316 includes two opposed ends, both of which are open. The light sensor 318 is mounted to one of the two longitudinally opposed ends of the permeable material body 316 and is in optical communication with the porous medium solution contained in the measuring cavity. In the embodiment shown, two light transmitters 354, 355 extend laterally along an outer wall of the sensing portion 314 and are mounted thereon. A first one of the light transmitters can be an illumination light transmitter 354, such as an optical fiber, while a second one of the light transmitters can be a resulting light transmitter 355, such as an optical fiber or an electric data transmitter. Thus, in the embodiment shown, the light source generates illumination light that travels through the illumination light transmitter 354 and illuminates the porous medium solution contained inside the measuring cavity at one end thereof. The light sensor 318 can then collect and detect the resulting light, such as the unabsorbed light, and the resulting light can travel through the resulting light transmitter 355 to be transmitted for instance to a data transmitter (or, in an alternate embodiment, to a real-time data transmitter), for the determination of the at least one ionic compound concentration based on the detected resulting light signal.

It is to be understood by a person skilled in the art that in the embodiment shown, the illumination light transmitter 354 is in optical communication with the light source and comprises a portion extending within the housing 312. Similarly, the resulting light transmitter 355 can also comprise a portion extending within the housing 312 such that an end opposed to the light sensor 318 can be connected to the real-time data transmitter. As mentioned hereinabove in relation to the embodiment shown in FIGS. 5A and 5B, the resulting light transmitter 355 can also be an electric data transmitter, for instance when the conversion of the resulting light into an electrical signal is performed in close proximity of the light sensor 318.

Figure 7:
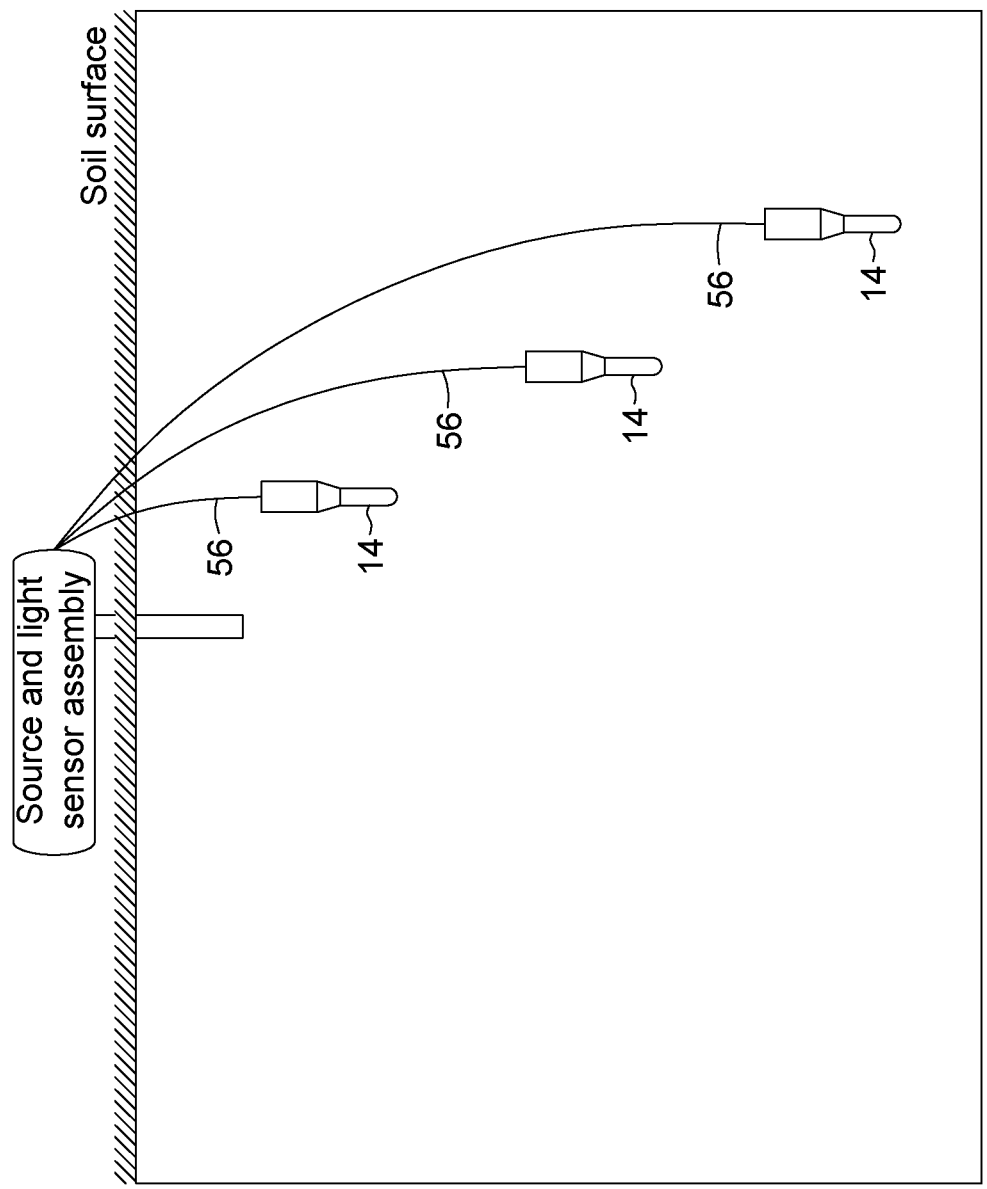
FIG. 7 is a schematic representation of a combination of three ionic concentration-measuring devices in accordance with another embodiment, the three ionic concentration-measuring devices being connected to a single light assembly that includes a light source and a light sensor, wherein each one of the ionic concentration-measuring devices includes a respective sensing portion and a light transmitter.

In some implementations and with reference to FIG. 7, there is shown a combination of ionic concentration-measuring devices connected to a single assembly including a light source and a light sensor. In the embodiment shown, each one of the ionic concentration-measuring devices includes a respective sensing portion and a light transmitter. Each one of the three ionic concentration-measuring devices is provided at a different depth in the soil, which can contribute to facilitate the collection of data representative of a larger volume of porous medium.

It is to be noted that the ionic concentration-measuring device can be configured to overcome some challenges typically associated with determining the ionic concentration of an ionic compound in a porous medium solution. Two non-limitative examples of such challenges are the presence of gas bubbles in the measuring cavity 24, 124 and microbial growth within the measuring cavity 24, 124.

Referring to FIGS. 1 to 6 and as mentioned previously, gas bubbles (which can result of the presence of air) can form in the measuring cavity 24, 124 (when referring to the measuring cavity hereinbelow, it is to be understood by the person skilled in the art that reference is also made to the measuring cavity defined in the permeable material body 216, 316 of the ionic concentration-measuring device 210, 310 shown in FIGS. 5 and 6, respectively), for instance along the inside wall of the measuring cavity 24, 124, in the measuring cavity 24, 124 itself, and/or on the surface of the distal end 26 of the light sensor 18 or on the surface of the optical fibers 154, 155 that are in optical communication with the light sensor 118, since the gap between the inside wall of the measuring cavity 24, 124 and the light sensor 18 or the optical fibers 154, 155 can be relatively narrow. In some implementations, gas bubbles can potentially impact the ionic concentration measurements, for instance by altering the continuity of the porous medium solution film, which can affect the diffusion of some ionic compounds through the permeable material body 16, 116, 216, 316. Thus, in some embodiments, the ionic concentration-measuring devices 10, 110, 210, 310 described herein can include various optional features in order to avoid the formation of gas bubbles in the measuring cavity 24, 124 or to facilitate their evacuation therefrom. For instance, in some embodiments, surfactants can be used, micro-blades can be positioned such that gas bubbles are not formed and/or are evacuated towards the proximal end 20, 120, 220 of the permeable material body 16, 116, 216, and/or a purge system using a micro-pump can be integrated into the ionic concentration-measuring device 10, 110, 210, 310 to improve the circulation of the porous medium solution and hence avoid the formation of gas bubbles in the measuring cavity 24, 124. The purge system can also facilitate the replacement of the content of the measuring cavity 24, 124. In other embodiments, a vibratory system, using mechanical or ultrasound vibrations, can also be integrated to the ionic concentration-measuring device 10, 110, 210, 310 to facilitate the displacement of the gas bubbles and avoid them being trapped in the measuring cavity 24, 124.

Still referring to FIGS. 1 to 6, given the relatively small dimensions of the permeable material body 16, 116, 216, 316 and the corresponding measuring cavity 24, 124 (when referring to the measuring cavity hereinbelow, it is to be understood by the person skilled in the art that reference is also made to the measuring cavity defined in the permeable material body 216, 316 of the ionic concentration-measuring device 210, 310 shown in FIGS. 5 and 6, respectively), a relatively small volume of porous medium solution can be contained therein. In some implementations, this smaller volume of porous medium solution, which includes variable amounts of organic matter and minerals, can lead to the formation of biofilms on the distal end 26 of the light sensor 18 or on the surface of the optical fibers 154, 155, and can also lead to microbial growth within the measuring cavity 24, 124, which can have an impact of the accuracy of the ionic concentration measurements taken by the light sensor 18, 118, 218, 318. In some embodiments, the purge system described hereinabove, by facilitating the replacement of the porous medium solution contained in the measuring cavity 24, 124, can also facilitate the cleaning of the measuring cavity 24, 124 for instance by allowing the replacement of the porous medium solution by a disinfecting solution or by a sterile solution which in turn can contribute to the reduction of microbial growth. In other embodiments, the light source can also be used to emit at wavelengths allowing disinfection of the porous medium solution. For instance, the light source can emit in the UV region of the light spectrum at wavelengths between about 200 and about 300 nm, and, in an embodiment, between about 240 and about 280 nm, periodically and outside measuring periods to disinfect the porous medium solution and the measuring cavity 24, 124.

Experimental Results

Figure 8:
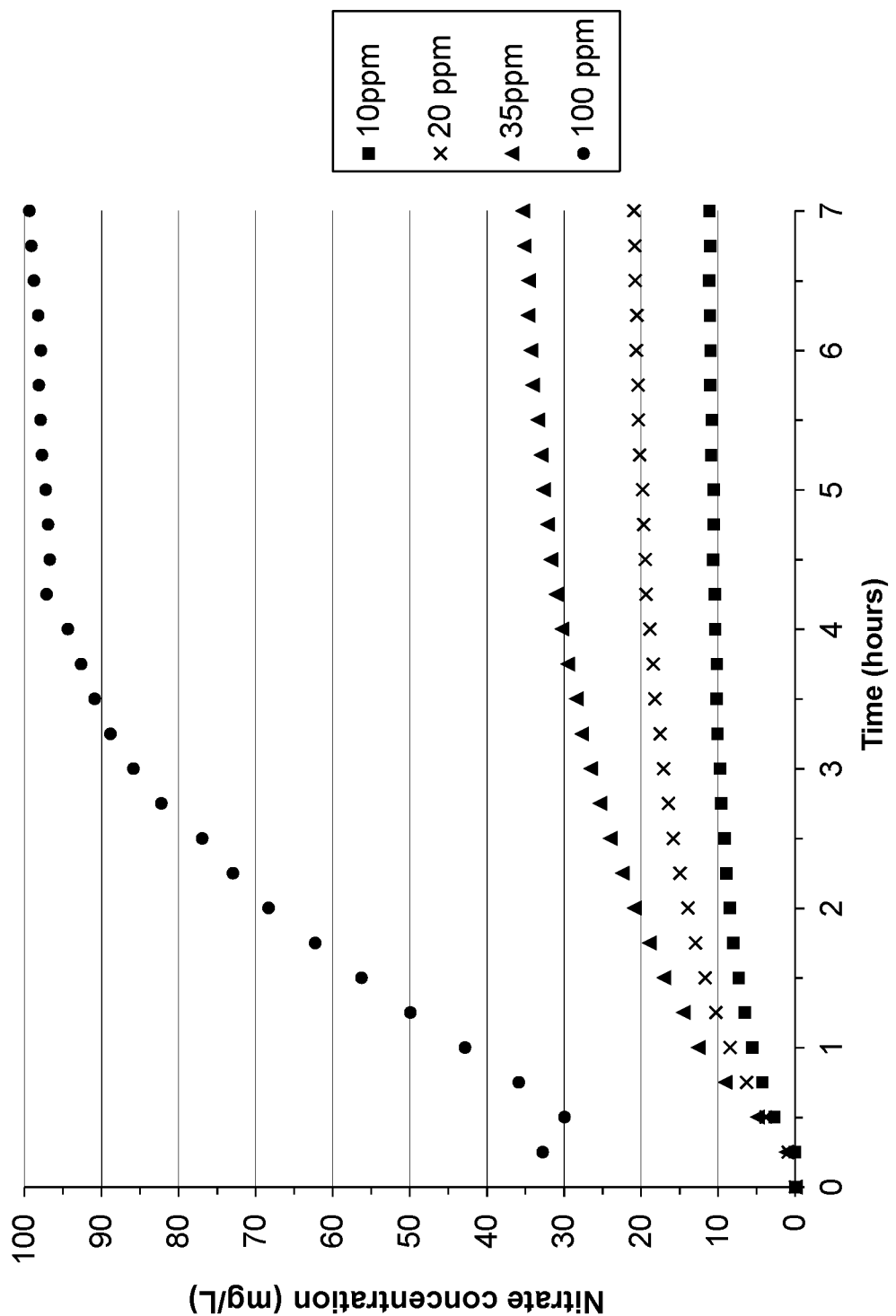
FIG. 8 is a graph showing variations of concentrations of nitrate ions as a function of time, i.e., a passive diffusion kinetic graph, for an ionic concentration-measuring device having a tubular shape, the ionic concentration-measuring device having a sensor portion having an inside width of 3 mm, an inside length of 20 mm, an outside width of 6 mm and an outside length of 25 mm, for various concentrations of nitrate ions.

Referring now to FIG. 8, there is provided a graph showing nitrate concentrations measured with an ionic concentration-measuring device as described herein, as a function of time. The ionic concentration-measuring device used for the experiments had a porous material body having tubular shape, and the dimensions of the porous material body were as follows: inside width of 3 mm, inside length of 20 mm, outside width of 6 mm, and outside length of 25 mm.

Four experiments were conducted in parallel. For each experiment, a different solution having a known concentration of nitrates was used. The four different concentrations of nitrates were 10 ppm, 20 ppm, 35 ppm and 100 ppm. The objective on the experiments was to evaluate the time required to reach equilibrium for each of the four different solutions. In order to do so, the sensing portion of the ionic concentration-measuring device was first saturated with deionized water, and then immersed in one of the four solutions. Data was collected every fifteen minutes, for up to seven hours.

The graph shows that the lower the concentration of nitrates in the solution, the shorter it takes to reach equilibrium. For the solution having a concentration of nitrates of 10 ppm, the equilibrium was reach after approximately three hours following immersion of the sensing portion in the solution. For the solutions having a concentration of nitrates of 20 ppm, 35 ppm and 100 ppm, the equilibrium was reached after approximately four hours following immersion of the sensing portion in the solution.

Figure 9:
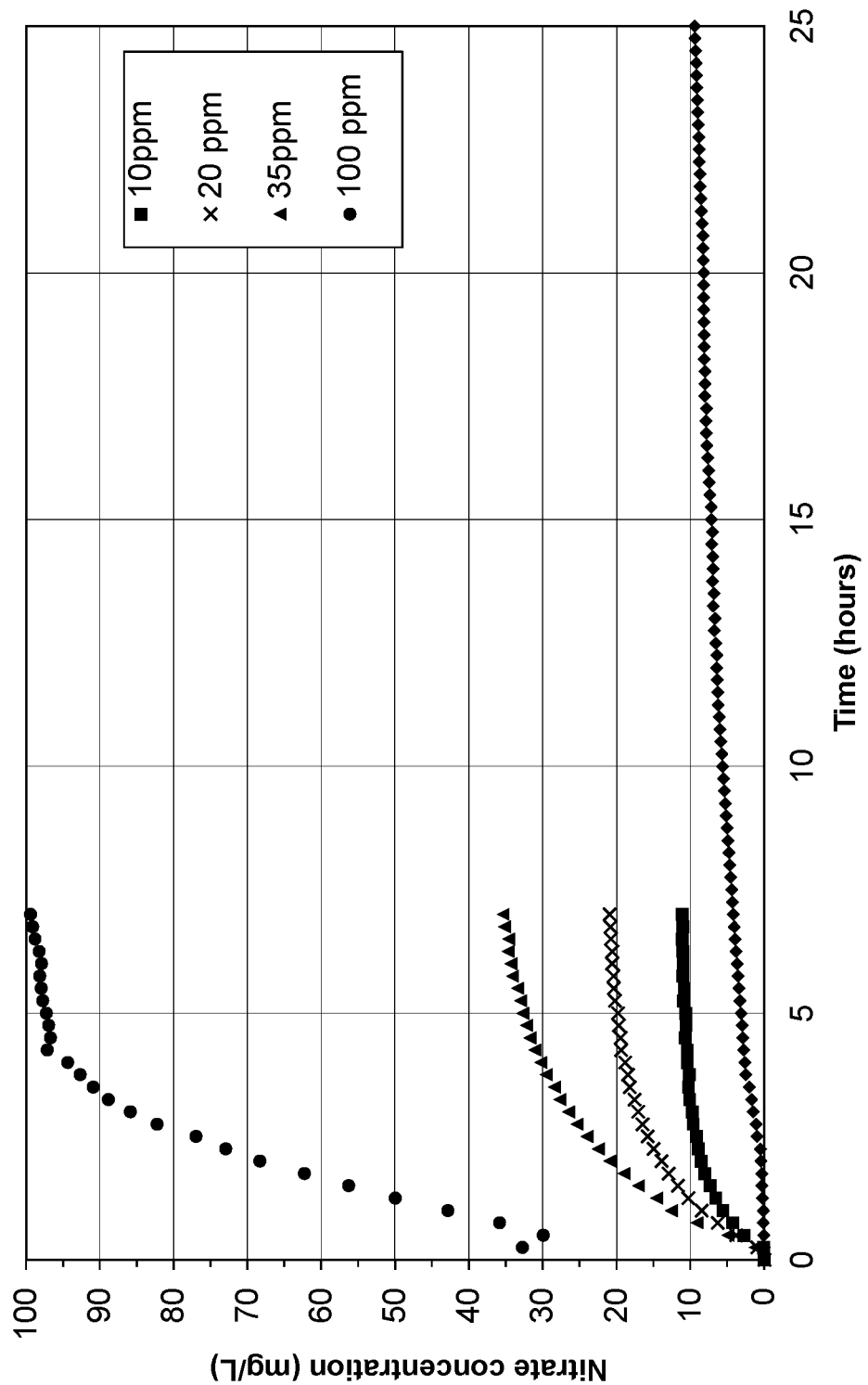
FIG. 9 is a graph showing the combination of the passive diffusion kinetic graph shown in FIG. 8 and a passive diffusion graph obtained with an ionic concentration-measuring device as known in the art having an inside width of 3 mm, an inside length of 40 mm, an outside width of 19 mm and an outside length of 50 mm.

The short period of time observed to reach equilibrium is expected to be the result of the miniaturisation of the ionic concentration measuring device. The effect of the miniaturisation of the ionic concentration-measuring device compared to a non-miniaturised ionic concentration-measuring device having larger dimensions as known in the art can be seen on FIG. 9. In FIG. 9, an additional equilibrium curve is shown for an ionic concentration-measuring device having an inside width of 3 mm, an inside length of 40 mm, an outside width of 19 mm, and an outside length of 50 mm. The sensing portion of the non-miniaturised ionic concentration-measuring device was first immersed in deionised water, and then immersed in a solution having a nitrate concentration of 10 ppm. The graph shows that approximately 25 hours is required to reach equilibrium, compared to three hours for the miniaturised ionic concentration device, as mentioned above.

Figure 10:
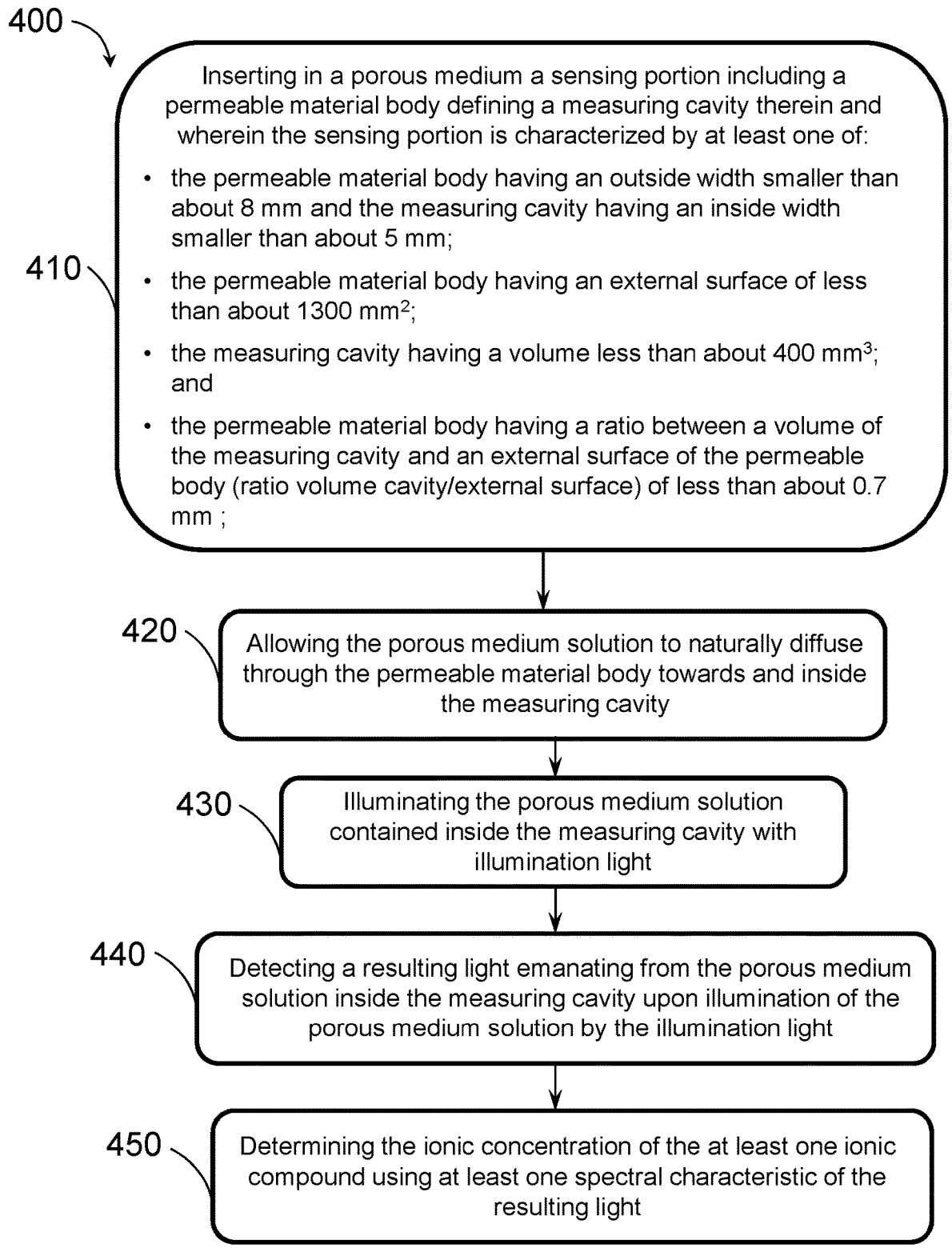
FIG. 10 is a flowchart depicting a method for measuring in situ an ionic concentration of at least one ionic compound in a porous medium solution contained in a porous medium in accordance with an embodiment.

In accordance with a second aspect and with reference to FIG. 10, there is provided a method 400 for measuring in situ an ionic concentration of at least one ionic compound dissolved in a porous medium solution using the ionic concentration-measuring device described herein. The method 400 includes the following steps.

As mentioned hereinabove, the porous medium solution is a solution that is contained in the pores of the porous medium. To measure the ionic concentration of an ionic compound dissolved in the porous medium solution, a sensing portion including a permeable material body is inserted into the porous medium 410. The permeable material body can be inserted into the porous medium for instance manually or using an automated system, or by any other suitable method. In an embodiment, the permeable material body is inserted into the porous medium such that it can be totally surrounded by the porous medium. As mentioned above, the permeable material body defines a measuring cavity therein. In some implementations, the permeable material body has an inside width of less than about 5 mm and an outside width of less than about 8 mm. In other implementations, the permeable material body has a measuring cavity having a volume of less than 400 mm$^3$, or a ratio [volume cavity/external surface] of less than 0.7 mm. In yet other implementations, the external surface of the permeable material body is less than about 1300 mm$^2$.

Once the permeable material body is inserted into the porous medium, the porous medium solution is allowed to diffuse through the permeable material towards and into the measuring cavity 420. This step is a passive transport step during which the porous medium solution naturally diffuses, i.e. without artificial intervention, into the measuring cavity through the pores of the permeable material body. In some embodiments, the porous medium solution within the measuring cavity is allowed to equilibrate relative to the porous medium solution contained in the porous medium. In some implementations, the period of time required for the porous medium solution within the measuring cavity to reach equilibration relative to the porous medium solution contained in the porous medium can be from about one hour to a few days, for instance 3 to 5 days. The period of time can depend on various parameters, such as the dimensions of the sensing portion, the dimensions of the permeable material body, or the dimensions of the complete ionic concentration-measuring device. The period of time can also depend on the water content of the soil (also referred to as "humidity"), i.e. when the soil is dryer, the period of time to reach equilibrium can be longer. The equilibration of the solution within the measuring cavity relative to the porous medium solution contained in the porous medium corresponds to the ionic equilibration of the various ionic compounds dissolved in the porous medium solution, such that the ionic concentration of the solution to be measured in the measuring cavity is representative of the actual ionic concentration in the porous medium solution. This aspect can be facilitated by the relatively small dimensions of the permeable material body, since equilibration can happen at a faster rate when only a small volume of solution to be measured is required to equilibrate.

The porous medium solution within the measuring cavity is then illuminated with an illumination light 430. In an embodiment, the illumination light is emitted by a light source emitting in the UV region of the light spectrum. In other embodiments, the light source is a light source emitting in the IR region or the NIR region of the light spectrum. The light source can also emit excitation light, which may pass through a filter to induce fluorescence, phosphorescence or chemiluminescence of the porous medium solution contained in the measuring cavity. The illumination light can be chosen according to the ionic compound for which the ionic concentration is to be measured. As mentioned above, depending on the ionic compound to be detected and/or the concentration of the ionic compound to be measured, the light source can be a light source such as a light emitting diode emitting over a narrower spectral range. Alternatively, the light source can be one of solid-state lighting including lasers, organic LEDs (OLEDs), incandescent lighting, halogen lighting, fluorescent light, infrared heat emitters, and discharge lighting. In an embodiment, if nitrate ions concentrations in a porous medium solution are to be measured, a light source emitting at least in the UV region of the light spectrum can be chosen, and the absorbance spectrum can be evaluated at wavelengths ranging between 200 nm and 240 nm, and in particular, at a peak wavelength of 220 nm.

As a result of the interaction of the medium porous solution inside the measuring cavity with the illumination light, a resulting light emanating from the porous medium solution is detected 440. The detection of the resulting light can be performed by a light sensor as described herein. The light sensor can measure for instance unabsorbed light resulting from reflection, transmission, transmittance, interference, or scattering, and/or light emitted through physical mechanisms, such as luminescence, photoluminescence, fluorescence, phosphorescence, and the like.

In an embodiment, the porous medium solution absorbs at least a portion of the illumination light inside the measuring cavity, and at least a portion of the illumination light thus remains as unabsorbed light. The unabsorbed light is collected and detected, for instance using a light sensor such as a spectrophotometer, according to known methods.

In some embodiments, the resulting light can be collected directly through the light sensor. In other embodiments, when the light sensor is contained in the housing or in the measuring cavity and adjacent to the illumination light transmitter, the resulting light can be collected through a distal end of a resulting light transmitter, following the reflection of the illumination light on a reflector positioned in the measuring cavity.

In some embodiments, the resulting light is measured at a given wavelength relative to a reference wavelength, for instance when parasitic absorption of the illumination signal by inorganic and/or organic substances present in various concentrations in the porous medium solution occurs. The inorganic and/or organic substances can be for instance humic and/or fulvic acids. In such embodiments, to compensate for this parasitic absorption of the illumination signal and when concentrations of nitrate ions are to be determined, the absorbance of the porous medium solution can be measured in the range from 200 nm to 240 nm and more specifically at a peak wavelength of 220 nm, relative to a given reference wavelength suitable to correct the parasitic absorption. The reference wavelength can be for instance in the range from 240 nm to 300 nm, and more specifically at a peak wavelength of 260 nm, a value at which nitrate ions do not absorb. This method is described in further detail in the non-patent literature document titled "A simple method for the determination of nitrate in potassium chloride extracts from forest soils", 2010, authored by Kaneko et al. Of course, other suitable methods can be used in other implementations to mitigate the parasitic absorption effects.

Then, the ionic concentration of the at least one ionic compound in the porous medium solution is determined, based on at least one spectral characteristic of the unabsorbed light 450. For instance, in the embodiment where the spectrophotometer is used, the amount of unabsorbed light measured by the spectrophotometer can be linearly or non-linearly correlated (e.g. logarithmically) to the absorbance of the porous medium solution being measured. The ionic concentration of the at least one ionic compound in the porous medium solution can be then determined according to the Beer-Lambert law, which states that the concentration of an absorbing solution is proportional to the absorbance at the given wavelength.

In another embodiment using an optical probe including a data treatment unit, which in turn includes a processor and/or related electrical circuitry, an electric signal generated by the light sensor can be processed to obtain an ionic concentration using, for example, a calibration equation and/or an appropriate theoretical or empirical model(s).

It will be appreciated that the methods described herein may be performed in the described order, or in any suitable order.

Several alternative embodiments and examples have been described and illustrated herein. The embodiments of the ionic concentration-measuring devices described hereinabove are intended to be exemplary only. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the wall assembly and the concrete containment wall assembly may be embodied in other specific forms without departing from the central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind. The scope of the invention is therefore intended to be limited solely by the scope of the appended claims.

What is claimed is:

1. An ionic concentration-measuring device for autonomously measuring an ionic concentration of at least one ionic compound in a porous medium solution contained in a porous medium, the device comprising:
    a sensing portion including a permeable material body defining a measuring cavity therein and being insertable in the porous medium on site to allow the porous medium solution to naturally diffuse into the measuring cavity through the permeable material body, wherein the sensing portion includes at least one of:
        the permeable material body having an outside width smaller than about 8 mm and the measuring cavity having an inside width smaller than about 5 mm; or
        the permeable material body having an external surface of less than about 1300 mm$^2$; or
        the measuring cavity having a volume less than about 400 mm$^3$; or
        the permeable material body having a ratio between a volume of the measuring cavity and an external surface of the permeable material body (ratio volume cavity/external surface) of less than about 0.7 mm;
    a housing coupled to the permeable material body and at least partially insertable in the porous medium;
    a light source configured to generate illumination light to illuminate the porous medium solution contained inside the measuring cavity; and
    a light sensor configured to detect a resulting light emanating from the porous medium solution contained inside the measuring cavity upon illumination of the porous medium solution by the illumination light, the resulting light having at least one spectral characteristic indicative of the ionic concentration of the at least one ionic compound in the porous medium solution; and
    a real-time data transmitter operatively connected to the light sensor and configured to continuously transmit real-time data based on the resulting light;
    wherein at least one of the light source and the light sensor is mounted onto or received within the housing.

2. The ionic concentration-measuring device of claim 1, wherein the sensing portion includes at least one of:
    the outside width of the permeable material body is between about 8 mm and about 6 mm, and the inside width of the measuring cavity is between about 3 mm and about 5 mm; or
    the external surface of the permeable material body is less than about 700 mm$^2$; or
    the volume of the measuring cavity is between about 400 mm$^3$ and about 200 mm$^3$; or
    the ratio volume cavity/external surface of the permeable material body is between about 0.7 mm and about 0.3 mm.

3. The ionic concentration-measuring device of claim 1, wherein the housing is further configured to contain the real-time data transmitter.

4. The ionic concentration-measuring device of claim 3, further comprising an optical probe mounted to the housing with the light sensor and the light source being contained in the optical probe.

5. The ionic concentration-measuring device of claim 1, further comprising at least one electric data transmitter in optical communication with the light sensor to allow the light sensor to detect the resulting light emanating from the porous medium solution contained inside the measuring cavity, the electric data transmitter being configured to convert the resulting light to an electrical signal to be processed by a processor, the electrical signal being indicative of and convertible into the ionic concentration.

6. The ionic concentration-measuring device of claim 1, wherein the light source emits in a visible, near-infrared, infrared, or ultraviolet range of the light spectrum to illuminate the porous medium solution contained inside the measuring cavity and the resulting light is unabsorbed light resulting from at least one of reflection, transmission, transmittance, interference and scattering.

7. The ionic concentration-measuring device of claim 1, wherein the light source emits an excitation light to induce at least one of fluorescence, phosphorescence luminescence, photoluminescence or chemiluminescence of the porous medium solution contained in the measuring cavity and the resulting light is emanating from at least one of fluorescence, phosphorescence luminescence, photoluminescence or chemiluminescence.

8. An autonomous method for measuring in situ an ionic concentration of at least one ionic compound in a porous medium solution contained in a porous medium, the method comprising the steps of:
  inserting, in the porous medium, a sensing portion including a permeable material body defining a measuring cavity therein and wherein the sensing portion includes at least one of:
    the permeable material body having an outside width smaller than about 8 mm and the measuring cavity having an inside width smaller than about 5 mm; or
    the permeable material body having an external surface of less than about 1300 $mm^2$; or
    the measuring cavity having a volume less than about 400 $mm^3$; or
    the permeable material body having a ratio between a volume of the measuring cavity and an external surface of the permeable material body (ratio volume cavity/external surface) of less than about 0.7 mm;
  allowing the porous medium solution to naturally diffuse through the permeable material body towards and inside the measuring cavity;
  illuminating the porous medium solution contained inside the measuring cavity with illumination light from a light source;
  detecting a resulting light emanating from the porous medium solution contained inside the measuring cavity by a light sensor upon illumination of the porous medium solution by the illumination light;
  wherein at least one of the light source and the light sensor is mounted onto or received within a housing coupled to the permeable material body and that is at least partially insertable in the porous medium; or
  wherein the light sensor is mounted onto an outer surface of the permeable body; and
  continuously determining in real-time the ionic concentration of the at least one ionic compound using at least one spectral characteristic of the resulting light.

9. The method of claim 8, wherein illuminating the porous medium solution contained inside the measuring cavity comprises generating illumination light using a light source, the light source emitting light in a visible, near-infrared, infrared, or ultraviolet range of the light spectrum.

10. The method of claim 9, wherein generating illumination light comprises emitting excitation light to induce to induce at least one of fluorescence, phosphorescence luminescence, photoluminescence or chemiluminescence of the porous medium solution contained in the measuring cavity.

11. The method of claim 9, wherein generating illumination light using the light source comprises operatively connecting at least one illumination light transmitter to the light source to direct the illumination light towards the porous medium solution.

12. The method of claim 8, wherein detecting the resulting light is performed using a light sensor.

13. The method of claim 12, wherein detecting the resulting light further comprises reflecting the illumination light on a reflector positioned inside the measuring cavity to direct the resulting light towards the light sensor.

14. The method of claim 12, wherein detecting the resulting light comprises operatively connecting at least one resulting light transmitter to the light sensor to detect the resulting light emanating from the porous medium solution contained inside the measuring cavity.

15. The method of claim 12, wherein detecting the resulting light comprises detecting the resulting light as real-time data to the light sensor using an electrical data transmitter, and converting the real-time data into an electrical signal to be processed by a processor, the electrical signal being indicative of and convertible into the ionic concentration.

16. An ionic concentration-measuring device for autonomously measuring an ionic concentration of at least one ionic compound in a porous medium solution contained in a porous medium, the device comprising:
  a sensing portion including a permeable material body defining a measuring cavity therein and being insertable in the porous medium on site to allow the porous medium solution to naturally diffuse into the measuring cavity through the permeable material body, wherein the sensing portion is characterized by at least one of:
    the permeable material body having an outside width smaller than about 8 mm and the measuring cavity having an inside width smaller than about 5 mm;
    the permeable material body having an external surface of less than about 1300 $mm^2$;
    the measuring cavity having a volume less than about 400 $mm^3$; or
    the permeable material body having a ratio between a volume of the measuring cavity and an external surface of the permeable material body (ratio volume cavity/external surface) of less than about 0.7 mm;
  a housing coupled to the sensing portion and at least partially insertable in the porous medium;
  a light source configured to generate illumination light to illuminate the porous medium solution contained inside the measuring cavity;
  a light sensor mounted onto an outer surface of the permeable material body and being configured to detect a resulting light emanating from the porous medium solution contained inside the measuring cavity upon illumination of the porous medium solution by the illumination light, the resulting light having at least one spectral characteristic indicative of the ionic concentration of the at least one ionic compound in the porous medium solution; and
  a real-time data transmitter operatively connected to the light sensor and configured to continuously transmit real-time data based on the resulting light.

17. The ionic concentration-measuring device of claim 16, further comprising:
  at least one illumination light transmitter operatively connected to the light source to direct the illumination light towards the porous medium solution contained inside the measuring cavity for illuminating same; and/or
  at least one resulting light transmitter operatively connected to the light sensor to allow the light sensor to detect the resulting light emanating from the porous medium solution contained inside the measuring cavity.

18. The ionic concentration-measuring device of claim 17, wherein the at least one illumination light transmitter and/or the at least one resulting light transmitter has a distal end located inside the measuring cavity or extends laterally along at least a section of the sensing portion and is mounted thereon.

19. The ionic concentration-measuring device of claim 17, wherein the at least one illumination light transmitter and/or the at least one resulting light transmitter comprises an optical fiber or an electric data transmitter.

20. The ionic concentration-measuring device of claim 17, further comprising a reflector positioned inside the measuring cavity to reflect at least one of the illumination light and the resulting light to be detected and direct the at least one of the illumination light and the resulting light to the light sensor.

21. The ionic concentration-measuring device of claim 16, wherein the light sensor is mounted to one of two longitudinally opposed ends of the permeable material body.

22. The ionic concentration-measuring device of claim 16, wherein the light sensor is mounted to the distal end of the permeable material body.

23. The ionic concentration-measuring device of claim 16, wherein the light source emits in a visible, near-infrared, infrared, or ultraviolet range of the light spectrum to illuminate the porous medium solution contained inside the measuring cavity and the resulting light is unabsorbed light resulting from at least one of reflection, transmission, transmittance, interference and scattering.

24. The ionic concentration-measuring device of claim 16, wherein the light source emits an excitation light to induce at least one of fluorescence, phosphorescence luminescence, photoluminescence and chemiluminescence of the porous medium solution contained in the measuring cavity and the resulting light is emanating from at least one of fluorescence, phosphorescence luminescence, photoluminescence and chemiluminescence.

* * * * *